(12) United States Patent
Fonte

(10) Patent No.: US 8,398,790 B2
(45) Date of Patent: *Mar. 19, 2013

(54) PROXIMALLY SELF-LOCKING LONG BONE PROSTHESIS

(75) Inventor: Matthew V. Fonte, Charlestown, MA (US)

(73) Assignee: MX Orthopedics, Corp., Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/352,112

(22) Filed: Jan. 17, 2012

(65) Prior Publication Data

US 2012/0123554 A1    May 17, 2012

Related U.S. Application Data

(60) Continuation of application No. 13/091,592, filed on Apr. 21, 2011, now Pat. No. 8,137,486, which is a continuation of application No. 12/424,885, filed on Apr. 16, 2009, now Pat. No. 7,947,135, which is a (Continued)

(51) Int. Cl.
*A61F 2/36* (2006.01)

(52) U.S. Cl. .................. 148/563; 148/561; 148/402

(58) Field of Classification Search ............ 148/563, 148/561, 402

See application file for complete search history.

(56) References Cited

U.S. PATENT DOCUMENTS

| 4,170,990 A | 10/1979 | Baumgart et al. ........ 128/92 B |
| 4,520,511 A | 6/1985 | Gianezio et al. ............. 3/1.913 |
| 4,522,200 A | 6/1985 | Stednitz ................. 128/92 BC |
| 4,665,906 A | 5/1987 | Jervis ..................... 128/92 YN |
| 4,756,711 A | 7/1988 | Mai et al. ...................... 623/23 |
| 4,776,337 A | 10/1988 | Palmaz ..................... 128/343 |

(Continued)

FOREIGN PATENT DOCUMENTS

| DE | 40 39 563 | 6/1991 |
| EP | 0 050 533 | 2/1985 |

(Continued)

OTHER PUBLICATIONS

Aamodt et al., "In Vivo Measurements Show Tensile Axial Strain in the Proximal Lateral Aspect of the Human Femur," The Journal of Bone and Joint Surgery, Inc., vol. 15, 1997, pp. 927-931.

(Continued)

*Primary Examiner* — Jie Yang
(74) *Attorney, Agent, or Firm* — Sunstein Kann Murphy & Timbers LLP

(57) ABSTRACT

A femoral stem hip implant for insertion into a surgically created aperture in a femur includes a monolithic femoral stem made of shape memory material. The stem is configured to be inserted into the aperture, has a proximal portion and a longitudinal axis. The shape memory material within the proximal portion has a cross-section perpendicular to the longitudinal axis. At least a portion of the shape memory material within the proximal portion is in a compressed state by application of a plurality of compressive forces at a temperature below an austenitic finish temperature of the shape memory material so that the cross-section expands through shape memory effect via the formation of austenite in response to a temperature increase after insertion into the aperture thereby causing a locking-force to be exerted against an inner surface of the aperture, the locking force being sufficient to stabilize the implant in the aperture.

2 Claims, 9 Drawing Sheets

Related U.S. Application Data division of application No. 12/054,678, filed on Mar. 25, 2008, now Pat. No. 8,062,378.

(60) Provisional application No. 60/919,969, filed on Mar. 26, 2007, provisional application No. 60/911,427, filed on Apr. 12, 2007, provisional application No. 60/911,633, filed on Apr. 13, 2007, provisional application No. 60/943,199, filed on Jun. 11, 2007, provisional application No. 60/991,952, filed on Dec. 3, 2007.

(56) References Cited

U.S. PATENT DOCUMENTS

| | | | |
|---|---|---|---|
| 4,792,339 A | 12/1988 | Tepi | 623/23 |
| 4,921,499 A | 5/1990 | Hoffman et al. | 623/16 |
| 4,997,444 A | 3/1991 | Farling | 623/16 |
| 5,035,712 A | 7/1991 | Hoffman | 623/16 |
| 5,120,175 A | 6/1992 | Arbegast et al. | 411/501 |
| 5,190,546 A | 3/1993 | Jervis | 606/78 |
| 5,219,363 A | 6/1993 | Crowninshield et al. | 623/23 |
| 5,507,826 A | 4/1996 | Besselink et al. | 623/22 |
| 5,584,695 A | 12/1996 | Lal Sachdeva et al. | 433/173 |
| 5,593,452 A | 1/1997 | Higham et al. | 623/23 |
| 5,702,482 A | 12/1997 | Thongpreda et al. | 623/23 |
| 5,858,020 A * | 1/1999 | Johnson et al. | 623/23.15 |
| 5,876,434 A | 3/1999 | Flomenbilt et al. | 623/1 |
| 5,876,446 A | 3/1999 | Agrawal et al. | 623/11 |
| 5,882,351 A | 3/1999 | Fox | 606/63 |
| 5,997,580 A | 12/1999 | Mastrorio et al. | 623/23.48 |
| 6,053,992 A | 4/2000 | Wu et al. | 148/402 |
| 6,063,442 A | 5/2000 | Cohen et al. | 427/250 |
| 6,162,257 A | 12/2000 | Gustilo et al. | 623/22.32 |
| 6,214,053 B1 | 4/2001 | Ling et al. | 623/23.11 |
| 6,287,310 B1 | 9/2001 | Fox | 606/63 |
| 6,299,448 B1 | 10/2001 | Zdrahala et al. | 433/173 |
| 6,344,055 B1 | 2/2002 | Shukov | 623/1.15 |
| 6,375,458 B1 * | 4/2002 | Moorleghem et al. | 433/2 |
| 6,379,390 B1 | 4/2002 | Advani et al. | 623/23.11 |
| 6,428,578 B2 | 8/2002 | White | 623/23.22 |
| 6,494,916 B1 | 12/2002 | Babalola et al. | 623/23.3 |
| 6,497,728 B2 | 12/2002 | Yong | 623/23.46 |
| 6,582,715 B1 | 6/2003 | Barry et al. | 424/422 |
| 6,682,568 B2 | 1/2004 | Despres, III et al. | 623/22.42 |
| 6,699,293 B2 | 3/2004 | White | 623/23.22 |
| 6,905,517 B2 | 6/2005 | Bonutti | 623/23.63 |
| 6,986,792 B2 | 1/2006 | McLean et al. | |
| 6,988,887 B2 | 1/2006 | Hansen et al. | 433/18 |
| 7,044,977 B2 | 5/2006 | Ferree | 623/23.25 |
| 7,097,664 B2 | 8/2006 | Despres, III et al. | 623/22.42 |
| 7,192,448 B2 | 3/2007 | Ferree | 623/18.11 |
| 7,214,765 B2 | 5/2007 | Ringeisen et al. | 528/502 D |
| 7,240,677 B2 | 7/2007 | Fox | 128/897 |
| 7,241,316 B2 | 7/2007 | Evans et al. | 623/23.51 |
| 7,282,165 B2 | 10/2007 | Williams, III et al. | 264/28 |
| 7,947,135 B2 | 5/2011 | Fonte | 148/563 |
| 8,062,378 B2 * | 11/2011 | Fonte | 623/23.26 |
| 2001/0018616 A1 | 8/2001 | Schwab | 623/23.17 |
| 2002/0004685 A1 | 1/2002 | White | 623/23.15 |
| 2002/0151984 A1 | 10/2002 | White | 623/23.22 |
| 2003/0130742 A1 | 7/2003 | Connelly et al. | 623/23.35 |
| 2004/0024469 A1 | 2/2004 | Ferree | 623/23.26 |
| 2004/0044391 A1 | 3/2004 | Porter | 623/1.1 |
| 2004/0111147 A1 | 6/2004 | Rabkin et al. | 623/1.15 |
| 2004/0117015 A1 | 6/2004 | Biscup | 623/16.11 |
| 2004/0117023 A1 | 6/2004 | Gerbec et al. | 623/18.11 |
| 2005/0080325 A1 | 4/2005 | Erickson | 600/395 |
| 2005/0142163 A1 * | 6/2005 | Hunter et al. | 424/423 |
| 2005/0187555 A1 | 8/2005 | Biedermann et al. | 606/72 |
| 2005/0288766 A1 | 12/2005 | Plain et al. | 623/1.12 |
| 2006/0217814 A1 | 9/2006 | Lambert et al. | 623/22.17 |
| 2007/0038219 A1 | 2/2007 | Matthis et al. | 606/72 |
| 2007/0050039 A1 | 3/2007 | Dietz et al. | 623/19.13 |
| 2007/0093908 A1 | 4/2007 | Despres, III et al. | 623/23.15 |
| 2007/0219641 A1 | 9/2007 | Dorr et al. | 623/22.42 |
| 2008/0021474 A1 | 1/2008 | Bonutti et al. | 606/64 |
| 2008/0161805 A1 | 7/2008 | Saravia et al. | 606/60 |
| 2008/0262629 A1 | 10/2008 | Fonte | 623/23.15 |

FOREIGN PATENT DOCUMENTS

| | | |
|---|---|---|
| EP | 0311 208 B1 | 3/1992 |
| EP | 0 403 028 | 9/1993 |
| EP | 0623 687 | 11/1994 |
| EP | 0728449 | 8/1996 |
| EP | 1205163 | 5/2002 |
| FR | 2483218 | 12/1981 |
| FR | 2862203 | 5/2005 |
| JP | 6045356 | 3/1985 |
| JP | 04187747 | 7/1992 |
| JP | 678989 | 3/1994 |
| WO | WO 93/08770 | 5/1993 |
| WO | WO 95/13757 | 5/1995 |
| WO | WO 97/20525 | 6/1997 |
| WO | WO 99/16478 | 4/1999 |
| WO | WO 00/09038 | 2/2000 |
| WO | WO 00/50100 | 8/2000 |
| WO | WO 02/056800 | 7/2002 |
| WO | WO 2007/028140 | 3/2007 |
| WO | WO 2008/109566 | 9/2008 |
| WO | WO 2008/130989 | 10/2008 |

OTHER PUBLICATIONS

Abdul-Kadir et al., "Finite element modelling of primary hip stem stability: The effect of interference fit," Journal of Biomechanics, vol. 41, 2008, pp. 587-594.

Albanese et al., "Bone remodeling in THA: A comparative DXA scan study between conventional implants and a new stemless femoral component. A preliminary report." Hip International, vol. 16 No. 1 (suppl. 3), 2006, pp. S9-S15.

Asgari et al., "Finite element modeling of a generic stemless hip implant design in comparison with conventional hip implants," Finite Elements in Analysis and Design, vol. 40 (2004) pp. 2027-2047.

Assad et al., "Porous Titanium-Nickel for Intervertebral Fusion in a Sheep Model: Part 2. Surface Analysis and Nickel Release Assessment," J. Biomed Mater Res. Part B: Appl. Biomater, 64B, pp. 121-129 (2003).

Barrabés et al., "Mechanical properties of nickel-titanium foams for reconstructive orthopaedics," Materials Science and Engineering, C 28 (2008) pp. 23-27.

Bayraktar et al., "*Comparison of the Elastic and Yield Properties of Human Femoral Trabecular and Cortical Bone Tissue,*" Journal of Biomechanics, vol. 37, pp. 27-35, (2004).

Béguec et al., "*The press-fit concept: an effective but demanding concept!*" Interact Surg, vol. 3, 2008, pp. 89-96.

Bergmann et al., "*Frictional Heating of Total Hip Implants. Part 2: finite element study,*" Journal of Biomechanics, vol. 34, pp. 429-435, (2001).

Bibee, "*Mapping Strain in Nanocrystalline Nitinol: an X-ray Diffraction Method,*" Department of Energy contract DE-AC02-76SF00515, 15 pages, (Aug. 19, 2005).

Bitsakos et al., "The effect of muscle loading on the simulation of bone remodelling in the proximal femur," Journal of Biomechanics, vol. 38 (2005), pp. 133-139.

Britton et al., "*Measurement of the Relative Motion Between an Implant and Bone under Cyclic Loading,*" Strain, vol. 40, 2004, pp. 193-202.

Bundy et al., "*Stress-enhanced ion release—the effect of static loading,*" Biomaterials, vol. 12, 1991, pp. 627-639.

Callaghan et al., "*The effect of femoral stem geometry on interface motion in uncemented porous-coated total hip prostheses. Comparison of straight-stem and curved-stem designs,*" Journal of Bone and Joint Surgery, vol. 74, No. 6, 1992, pp. 839-848.

Chao et al., "*Failure of analysis of a Ti6Al4V cementless Hip prosthesis,*" Engineering Failure Analysis, vol. 14, 2007, pp. 822-830.

Chao, Jesús, "*Is 7206 ISO standard enough to prove the endurance of femoral components of hip prostheses,*" Engineering Failure Analysis, vol. 15, 2008, pp. 83-89.

d'Imporzano et al., "*Minimally invasive total hip replacement,*" J. Orthopaed Traumatol, vol. 7, pp. 42-50, 2006.

Eiselstein et al., "*Review of Fatigue and Fracture Behavior in NiTi*," Proceedings of the Materials & Processes for Medical Devices Conference, Nov. 14-16, 2005, Boston, MA, pp. 135-147.

Ender et al., "*Cementless CUT femoral neck prosthesis: increased rate of aseptic loosening after 5 years*," Acta Orthopaedica, http://dx.doi.org/10.1080/1745367071001430, vol. 78, No. 5, pp. 616-621, 2007.

Engh C. A. et al., "Long-Term Results of Use of the Anatomic Meduallary Locking Prosthesis in Total Hip Arthroplasty," The Journal of Bone and Joint Surgery, (1997) vol. 79-A, No. 2, pp. 177-184.

Engh C.A. et al., "Evaluation of bone ingrowth in proximally and extensively porous-coated anatomic medullary locking prostheses retrieved at autopsy," The Journal of Bone and Joint Surgery, vol. 77, Issue 6, pp. 903-910 (1995).

Engh et al., "*Factors Affecting Femoral Bone Remodeling After Cementless Total Hip Arthroplasty*," The Journal of Arthroplasty, vol. 14, No. 5, 1999, pp. 637-644.

Falez et al., "*Perspectives on metaphyseal conservative stems*," J. Orthopaed Traumatol, vol. 9, pp. 49-54, 2008.

Fottnor et al., "*Biomechanical Evaluation of Two Types of Short-Stemmed Hip Prostheses Compared to the Trust Plate Prosthesis by Three-Dimensional Measurement of Micromotions*," Clinical Biomechanics, vol. 24, pp. 429-434, (2009).

Friesdorf et al., "*Musculoskeletal Loading and Pre-clinical Analysis of Primary Stability after Cementless Total Hip Arthroplasty in Vitro*," 148 pages, Oct. 25, 2004.

Gall et al., "*The role of texture in tension-compression asymmetry in polycrystalline NiTi*," International Journal of Plasticity, vol. 15, 1999, pp. 69-92.

Gall et al., "*Tension-Compression Asymmetry of the Stress-Strain Response in Aged Single Crystal and Polycrystaline NiTi*," Acta Mater, vol. 47. No. 4, 1203 pp. 1203-1217 (1999).

Gao et al., "*Experimental study on the Anisotropic Behavior of Textured NiTi Pseudoelastic Shape Memory Alloys*," Materials Science and Engineering, vol. A362, pp. 107-111, 2003.

Gebert et al., "*Influence of press-fit parameters on the primary stability of uncememted femoral resurfacing implants*," Medical Engineering & Physics, 2008, pp. 1-5.

Gheduzzi et al., "*A review of pre-clinical testing of femoral stem subsidence and comparison with clinical data*," Proc. IMechE, vol. 221, Part H: J. Engineering in Medicine, Jun. 2006, pp. 39-46.

Griza et al., "*Failure of analysis of uncemented total hip stem due to microstructure and neck stress riser*," Engineering Failure Analysis, vol. 15, 2008, pp. 981-988.

Gulow et al., "Kurzschäfte in der Hüftendoprothetik," Orthopäde, vol. 36 (2007) pp. 353-359.

Gulow et al., "Short-stemmed Endoprosthesis in Total Hip Arthroplasty," Orthopäde, vol. 36 (2007) pp. 353-359. (English Abstract).

Harman et al., "*Initial stability of uncemented hip stems: an in-vitro protocol to measure torsional interface motion*," Med. Eng. Phys., vol. 17, No. 3, 1995, pp. 163-171.

International Searching Authority, *International Search Report and Written Opinion*, International Application No. PCT/US2008/058094, dated Jul. 28, 2008, 9 pages.

James, B. et al., "Failure Analysis of NiTi Wires Used in Medical Applications," Journal of Failure Analysis Prevention, vol. 5(5), Oct. 2005, pp. 1547-7029.

James et al., "*Compressive Damage-Induced Cracking in Nitinol*," Proceedings of the International Conference on Shape Memory and Superelastic Technologies, Oct. 3-7, 2004, Kurhaus Baden-Baden, Baden-Baden, Germany, pp. 117-124.

Jasty et al, "The Contribution of the Nonporous Distal Stem to the Stability of Proximally Porous-coated Canine Femoral Components," The Journal of Arthroplasty, vol. 8, No. 1, (1993), pp. 33-40.

Jensen, Daniel M., "*Biaxial Fatigue Behavior of NiTi Shape Memory Alloy*," Thesis presented to Air Force Institute of Technology, 2005, pp. 1-101.

Joshi et al., "Analysis of a femoral hip prosthesis designed to reduce stress shielding," Journal of Biomechanics, 33 (2000) pp. 1655-1662.

Joshi et al., "*Analysis of a Femoral Hip Prosthesis Designed to Reduce Stress Shielding*," Journal of Biomechanics, vol. 33, pp. 1655-1662, (2000).

Kim et al., "*Development of a NiTi Actuator Using a Two-Way Shape Memory Effect Induced by Compressive Loading Cycles*," Sensors and Actuators, pp. 437-442 (2008).

Kim, Young-Hoo, M.D., "Cementless Total Hip Arthroplasty with a Close Proximal Fit and Short Tapered Distal Stem (Third-Generation) Prosthesis," The Journal of Arthroplastcy, vol. 17, No. 7 (2002) pp. 841-850.

Kropfl et al., "*Intramedullary Pressure and Bone Marrow Fat Extravasation in Reamed and Unreamed Femoral Nailing*," The Journal of Bone and Joint Surgery, vol. 17, 1998, pp. 261-268.

Kujala et al., "Bone modeling controlled by a nickel-titanium shape memory alloy intramedullary nail," Biomaterials, 23 (2002) pp. 2535-2543.

Kujala et al., "Comparison of the bone modeling effects caused by curved and straight nickel-titanium intramedullary nails," Journal of Materials Science: Materials in Medicine, 13 (2002) pp. 1157-1161.

Kujala, S., Academic Dissertation "Biocompatibility and Biomechanical Aspects of Nitinol Shape Memory Metal Implants," Univ. of Oulu (Nov. 7, 2003).

Laine et al., "*The Femoral Canal Fill of Two Different Cementless Stem Designs*," International Orthopaedics (SICOT), vol. 25, pp. 209-213, (2001).

Leali et al., "*The effect of a lateral flare feature on implant stability*," International Orthopaedics (SICOT), vol. 26, 2002, pp. 166-169.

Learnmonth, I.D., *Foreword*, Hip International, vol. 16, No. 1 (suppl. 3), p. S1, Wichtig Editore, 2006.

Lewandowska-Szumiel et al., "*Osteoblast response to the elastic strain of metallic support*," Journal of Biomechanics, vol. 40, 2007, pp. 554-560.

Liu et al., "*Twinning and detwinning of <0 1 1> type II twin in shape memory alloy*," Acta Materialia, vol. 51, 2003, pp. 5529-5543.

Liu et al., "*Asymmetry of Stress-Strain Curves Under Tension and Compression for NiTi Shape Memory Alloys*," Acta Mater, vol. 46. No. 12, pp. 4325-4338 (1998).

Machado, L.G. et al., "Medical applications of shape memory alloys," Brazilian Journal of Medical and Biological Research, (2003), 36: pp. 683-691.

Malchau et al., "*Long-term clinical and radiographic results of a fully porous-coated stem and a non-coated threaded cup [A prospective study of the Lord total hip prosthesis]*," Journal of Bone and Joint Surgery, pp. 3-17, (1995).

Mantovani, D., "Shape Memory Alloys: Properties and Biomedical Applications," Journal of Materials, (Oct. 2000).

Mazoochian et al., "*Proximal loading of the femur leads to low subsidence rates: first clinical results of the CR-stem*," Orthopaedics Trauma Surgery, vol. 127, Jun. 2007, pp. 397-401.

McKelvey et al., "*Fatigue-Crack Propagation in Nitinol, A Shape-Memory and Superelastic Endovascular Stent Material*," Journal of Biomedical Materials Research Part A, vol. 47, Issue 3, 1999, pp. 301-308.

McNamara et al., "*Relationship Between Bone-Prosthesis Bonding and Load Transfer in Total Hip Reconstruction*," J. Biomechanics, vol. 30, No. 6, 1997, pp. 621-630.

Meldrum, R.D. et al., "The strength of a cement acetabular locking mechanism," Journal of Arthroplasty, Sep. 2001 6 (6) pp. 748-752.

Miller et al., "*Stress-Induced Martenistic Phase Transformations in NiTi Shape Memory Alloys During Dynamic Loading*," Proceedings of ASMS '00, Nov. 5-10, 2000, Orlando FL, Los Alamos National Laboratory, pp. 1-11.

Monassevitch et al., "Biomedical Behavior of Nitinol Implants in Compressive Osteosynthesis," Proc. Int'l. Conf. Shape Memory and Superelastic Technologies, Oct. 3-7 pp. 615-620 (2004).

Moore, A.T., "The Self-Locking Metal Hip Prosthesis," Journal of Bone and Joint Surgery, 1957, vol. 39, pp. 811-827, 1957.

Morgan et al., "*Sensitivity of Multiple Damage Parameters to Compressive Overload in Cortical Bone*," Journal of Biomechanical Engineering, vol. 127, Aug. 2005, pp. 557-562.

Morrey et al., "*A conservative femoral replacement for total hip arthroplasty*," J. Bone Joint Surg., vol. 82-B, No. 7, pp. 952-958, 2000.

Munting et al., "Effect of a Stemless Femoral Implant for Total Hip Arthroplasty on the Bone Mineral Density of the Proximal Femur: A Prospective Longitudinal Study," The Journal of Arthroplasty, vol. 12, No. 4 (1997) pp. 373-379.

Munting et al., "*Fixation and Effect on Bone Strain Pattern of a Stemless Hip Prosthesis*," J. Biomechanics, vol. 28, No. 8, pp. 949-961, 1995.

N. Santori et al., "Proximal load transfer with a stemless uncemented femoral implant," J. Orthopaed Traumatol, (2006) 7:154-160.

O'Donnell, R., "Compressive osseointegration of modular endoprosthesis," Current Opinion in Orthopaedics, 18: pp. 590-603 (2007).

Pan et al., "*The Investigation of a Shape Memory Alloy Micro-Damper for MEMS Applications*," Sensors, vol. 7, 2007, pp. 1887-1900.

Pelton et al., "*Fatigue Testing of Diamond-Shaped Specimens*," Nitinol Devices & Components, 2003, pp. 1-9.

Perry et al., "Measurement of Deformation and Strain Nitinol," Experimental Mechanics, pp. 373-380 (Feb. 15, 2007).

Plietsch et al., "*Strength Differential Effect in Pseudoelastic NiTi Shape Memory Alloys*," Acta mater, vol. 45, No. 6, pp. 2417-2424 (1997).

Qian et al., "*Fretting wear behavior of superelastic nickel titanium shape memory alloy*," Tribology Letters, vol. 18, No. 4, Apr. 2005, pp. 463-475.

Rhalmi et al., "Spinal evaluation of porous nitinol particles: a short-term study in rabbits," Proc. 49$^{th}$ Annual Meeting of Orthopedic Research Society, (2003).

Robertson et al., "*Crystallographic Texture for Tube and Plate of the Superelastic/Shape-Memory Alloy Nitinol Used for Endovascular Stents*," Wiley InterScience, pp. 190-199 (Dec. 14, 2004).

Rudman et al., "*Compression or tension? The stress distribution in the proximal femur*," BioMedical Engineering OnLine, vol. 5, No. 12, 2006, pp. 1-7 http://www.biomedical-engineering-online.com/content/5/1/12.

S. Daly et al., "*Large Deformation of Nitinol Under Shear Dominant Loading*," Experimental Mechanics, 9 pages, (2008).

Salemyr et al., "*Good Results with an Uncemented Proximally HA-coated Stem in Hip Revision Surgery*," Acta Orthopaedica, vol. 79 (2), pp. 184-193, (2008).

Schiff et al., "*Galvanic corrosion between orthodontic wires and brackets in fluoride mouthwashes*," European Journal of Orthodontics, vol. 28, 2006, pp. 298-304.

Schuh et al., "*Second Generation (low modulus) Titanium Alloys in Total Hip Arthroplasty*," Mat.-wiss. u. Werkstofftech, vol. 38, No. 12, pp. 1003-1007, (2007).

Shabalovskaya, Svetlana A., "*Surface, corrosion and biocompatibility aspects of Nitinol as an implant material*," Bio-Medical Materials and Engineering, vol. 12, 2002, pp. 69-109.

Singh et al., "*Corrosion degradation and prevention by surface modification of biometallic materials*," J Mater Sci: Mater Med, vol. 18, 2007, pp. 725-751.

Smith-Adaline et al., "*Mechanical Environment Alters Tissue Formation Patterns During Fracture Repair*," Journal of Orthopaedic Research, vol. 22, pp. 1079-1085, (2004).

Soderberg et al., "*Compressive Training of the Shape Memory Alloy Washer*," JMEPEG, vol. 6, pp. 517-520, (Aug. 1997).

Speirs et al., "Influence of changes in stem positioning on femoral loading after THR using a short-stemmed hip implant," Clinical Biomechanics, vol. 22 (2007) pp. 431-439.

Spoerke et al., Elsevier Manuscript Draft: "A Bioactive Titanium Foam Scaffold for Bone Repair," submitted to Acta Biomaterialia, pp. 1-26, Jan. 2005.

Taylor et al., "*Determination of orthotropic bone elastic constants using FEA and modal analysis*," J. Biomechanics, vol. 35, pp. 767-773, 2002.

Thelen et al., "Mechanics considerations for microporous titanium as an orthopedic implant material," J. Biomedical Materials Research Part A, vol. 69, No. 4, pp. 601-610 (2004).

Udomkiat, P. et al., "Cementless Hemispheric Porous-Coated Sockets Implanted With Press-Fit Technique Without Screws: Average Ten-Year Follow-Up," The Journal of Bone & Joint Surgery, vol. 84-A, No. 7, Jul. 2002.

Vandygriff, E.L. et al., "Porous Shape Memory Alloys, Part I: Fabrication and Characterization," Proceedings of the American Society for Composites 15th, 2000.

Viceconti et al., "*Primary stability of an anatomical cementless hip stem: A statistical analysis*," Journal of Biomechanics, vol. 39, 2006, pp. 1169-1179.

Wang et al., "*The effect of grain orientation on the tensile-compressive asymmetry of polycrystalline NiTi shape memory alloy*," Werkstofftech, vol. 38, No. 4, 2007, pp. 294-298.

Wedemeyer et al., "*Digital templating in total hip arthroplasty with the Mayo stem*," Arch. Orthop. Trauma Surg., Springer-Verlag, 2007, 7 pages.

Weinans et al., "*Effects of Fit and Bonding Characteristics of Femoral Stems on Adaptive Bone Remodeling*," Journal of Biomechanical Engineering, vol. 116, Nov. 1994, pp. 393-400.

Westphal et al., "*Migration and cyclic motion of a new short-stemmed hip prosthesis—a biomechanical in vitro study*," Clinical Biomechanics, vol. 21, 2006, pp. 834-840.

Winwood et al., "*The importance of the elastic and plastic components of strain in tensile and compressive fatigue of human cortical bone in relation to orthopaedic biomechanics*," J Musculoskelet Neuronal Interact, vol. 6, No. 2, 2006, pp. 134-141.

Wu et al., "NiTiNb Plugs for Sealing High Pressure Fuel Passages in Fuel Injector Applications," Proceedings, International Conference on Shape Memory and Superelastic Technolgies, (2000) pp. 235.

Zimmer Brochure, "Alloclassic® Zweymuller™," 4 pages, 2003.

Centerpulse Brochure, "CLS Hip System: The standard of proximal press-fit design," 4 pages, 2002.

Zimmer Brochure, "Epoch Low-Modulus, Composite Structure Prosthesis," 8 pages, 2002.

Zimmer Brochure, "Mayo Conservative Hip Prosthesis," 6 pages, 1998.

ASTM International, Standard Specification for Femoral Prostheses-Metallic Implants, 6 pages, Oct. 2003.

Zimmer Brochure, "VerSys, Fiber Metal Taper Hip Prosthesis," 4 pages, 1997.

* cited by examiner

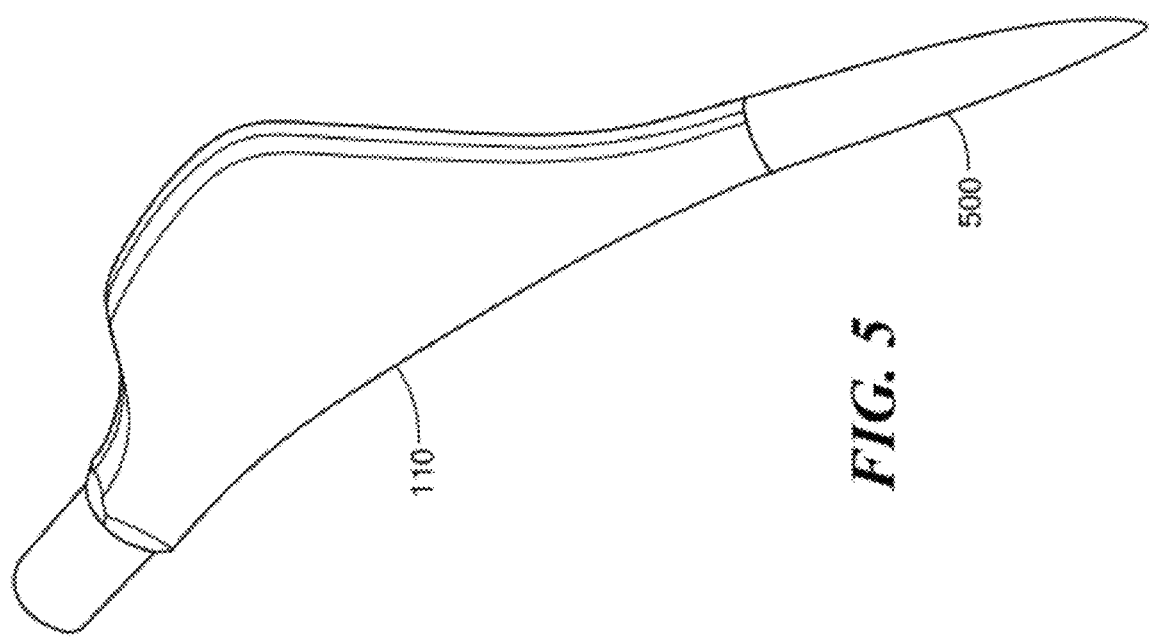
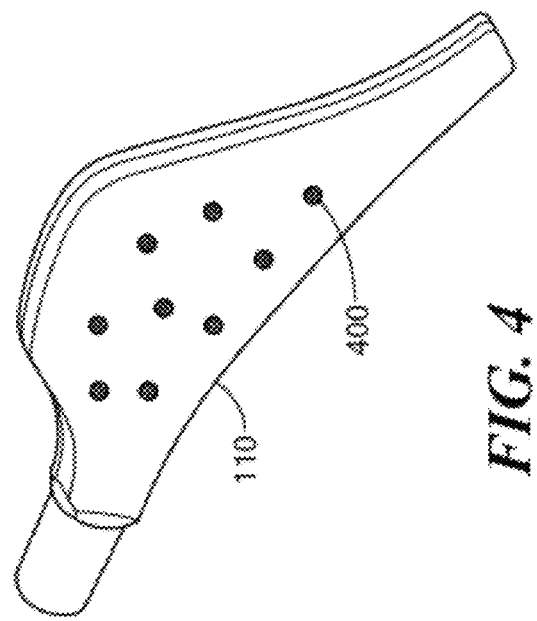

Hip Design A

Hip Design B

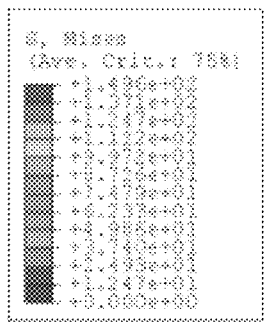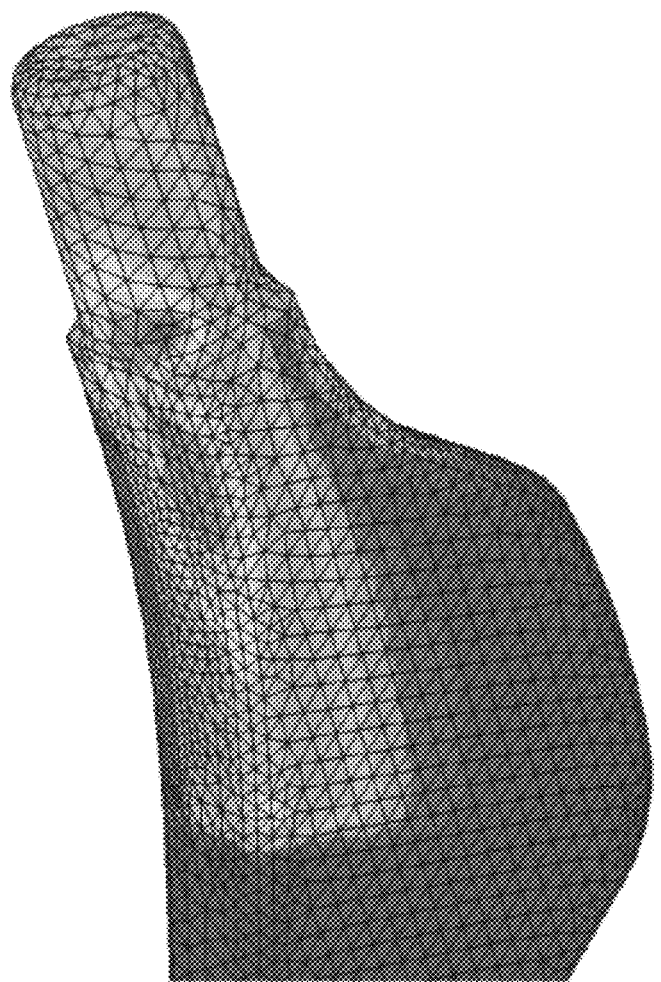
*FIG. 11*

PROXIMALLY SELF-LOCKING LONG BONE PROSTHESIS

CROSS REFERENCE TO RELATED APPLICATIONS

The present application is a continuation of U.S. patent application Ser. No. 13/091,592, filed on Apr. 21, 2011 now U.S. Pat. No. 8,137,486, which is a continuation of U.S. patent application Ser. No. 12/424,885, filed on Apr. 16, 2009, now U.S. Pat. No. 7,947,135, which in turn is a divisional of U.S. patent application Ser. No. 12/054,678, filed Mar. 25, 2008, now U.S. Pat. No. 8,062,378, which claims priority to U.S. Provisional Patent Application Ser. No. 60/919,969, filed Mar. 26, 2007, U.S. Provisional Patent Application Ser. No. 60/911,427, filed Apr. 12, 2007, U.S. Provisional Patent Application Ser. No. 60/911,633, filed Apr. 13, 2007, U.S. Provisional Patent Application Ser. No. 60/943,199, filed Jun. 11, 2007, and U.S. Provisional Patent Application Ser. No. 60/991,952, filed Dec. 3, 2007, the disclosures of which are hereby incorporated herein, in their entirety, by reference.

TECHNICAL FIELD

The invention generally relates to medical implants and, more particularly, the invention relates to materials, structures and methods of using medical implants.

BACKGROUND

Damage to a joint of a patient may result from a variety of causes, including osteoarthritis, osteoporosis, trauma, and repetitive overuse. Osteoarthritis is a condition characterized by damage of the joint cartilage and resulting inflammation and pain. The cause of hip osteoarthritis is not known for certain, but is thought to be "wear and tear" in most cases. Some conditions may predispose the hip to osteoarthritis; e.g., a previous fracture of the joint. In osteoarthritis of the hip, the cartilage cushion may be thinner than normal, leaving bare spots on the bone. Bare bone on the head of the femur grinding against the bone of the pelvic socket causes mechanical pain. Fragments of cartilage floating in the joint may cause inflammation in the joint lining, which may also cause pain. Rheumatoid Arthritis (R.A.) starts in the synovium and is mainly "inflammatory". The cause is not known; however, it is known that the condition leads to an eventual destruction of the joint cartilage. Bone next to the cartilage is also damaged; it becomes very soft, frequently making the use of an un-cemented implant impossible. Lupus is another form of hip arthritis that is mainly "inflammatory". Osteonecrosis is a condition in which part of the femoral head dies. This dead bone can not stand up to the stresses of walking. As a result, the femoral head collapses and becomes irregular in shape. The joint then becomes more painful. The most common causes of osteonecrosis are excessive alcohol use and excessive use of cortisone-containing medications.

Implanted prosthetics have been used to replace various components of an affected joint. For example, total hip joint replacement (arthroplasty) surgeries are becoming more prevalent. One common arthroplasty technique uses a cemented femoral implant (i.e., a prosthesis). Undesirably, cemented implants often loosen, causing pain and requiring subsequent surgeries. Alternatively, cementless implants often require an extended period of bone-ingrowth in order for a patient to regain full use of the joint. During the recovery period, the patient with a cementless implant is often required to use crutches or other weight-bearing mechanical assistance to avoid fully loading the implant.

For the structure of the femur prior to arthroplasty, the load distribution can be essentially resolved into an axial component, two bending moments and a torsional moment, which depend on leg stance. The distribution of these load components is changed after the arthroplasty. Conventional methods of prosthesis fixation allow for transfer of axial loads to the bone mainly through shear stresses at the bone-implant interface. (The muscles attached to the femur transfer load and moments as before the arthroplasty). The bending moment is effectively transferred to the bone, primarily through a contact between the prosthesis and the bone in two or more localized regions. In addition, the great disparity in the stiffness of a metallic prosthesis and the surrounding bone reduces bending displacements, changing the bending moment distribution in the surrounding bone.

Conventional femoral prostheses include an elongated stem for insertion into a surgically created cavity in a bone. The elongated stem may provide for accelerated integration of the prosthesis and an early recovery, but potentially at the expense of long-term stability. Because biomechanical forces will be transferred to distal regions of the implanted prosthesis (i.e., "distal bypass"), bone resorption may occur in more proximal portions of the bone—a process known as "stress shielding." This bone resorption is a consequence of a natural process in which bone remodels in response to applied stresses. Bone density tends to increase in response to applied stress and decrease in response to removal of stress. Proximal bone resorption, along with a levering effect of a long stem, may cause loosening of the prosthesis over time.

An additional source of implant failure results from acetabular wear particles, which induce an inflammatory response in the patient. The resulting chronic inflammation may cause bone loss through osteolysis.

A further source of cemented implant failure is through degradation of the cement over the course of several decades. For this reason, practitioners disfavor the use of cemented implants in younger people.

Most femoral implants are introduced by hammering the stem into an aperture in the bone to create an interference fit. This procedure carries a risk of fracturing the bone, which is estimated by some sources to be in the range of 1-3%.

Recently, "stemless" implants have been begun to be adopted in Europe. See, e.g., Santori, "Proximal load transfer with a stemless uncemented femoral implant" J. Ortopaed Traumatol (2006) 7:154-160. Stemless implants may avoid at least some stress shielding by selectively transferring loads to more proximal bone regions. However, because of inherently lower primary (initial) stability, these stemless implants may require a longer recovery period than conventional stemmed implants and patients must limit weight bearing (e.g., by using crutches) during recovery. Advani, U.S. Pat. No. 6,379,390, discloses a stemless hip prosthesis that includes a cable for wrapping around a reconstructed femur in order to secure the prosthesis.

The success of a hip replacement can be adversely affected by periprosthetic infection, which can have immense financial and psychological costs. Common measures, including the use of body exhaust systems, laminar airflow, prophylactic antibiotics, and various other precautions, have been successful in reducing the incidence of periprosthetic infection. Despite these measures, it is believed that deep infection still occurs after 1 to 5 percent of joint replacements. The incidence is even higher in some high risk patients, such as patients with diabetes, patients with remote history of infection, and patients with inflammatory arthropathies.

Orthopedic scientists have been attempting to design a biologically active implant surface that prevents periprosthetic infection. One strategy is to apply drugs to the surface of implants, such as cemented or cementless implants. Current cementless hip and knee implants, for example, are wedged into the femoral or tibial bone by means of a hammering the implant with a mallet to drive the implant into the pre-drilled bone cavity. A tight interference fit between the implant and femoral bone, however, may undesirably scrape and/or squeegee off any drugs applied to the surface of the implant stem.

Shape memory materials are known in the art. See, for example, Mantovi, D., "Shape Memory Alloys Properties and Biomedical Applications," Journal of Materials (2000). In particular, shape memory alloys, the most common of which is Nitinol, a nickel-titanium alloy, exist in a martensitic state below a first temperature and an austenitic state above a second temperature. Because the different states have different geometries, a temperature change can lead to a change in shape of an object made from shape memory material.

Nitinol exhibits various characteristics depending on the composition of the alloy and its thermal and work history. For example, the transition temperature or range may be altered. Nitinol can exhibit 1-way or 2-way shape memory effects. A 1-way shape-memory effect results in a substantially irreversible change upon crossing the transition temperature, whereas a 2-way shape-memory effect allows the material to repeatedly switch between alternate shapes in response to temperature cycling. Two-way shape-memory typically requires a cyclic working of the material; this is commonly performed by cyclically pulling on the material in tension. Additionally, Nitinol may be used in a pseudoelastic mode based on the formation of stress-induced martensite. Pseudoelastic Nitinol is typically employed at a temperature well above its transition temperature.

One common use of Nitinol in medical devices is its use in arterial stents. To this end, much research has been performed to test the life cycles and other wear properties of Nitinol wires. At least one study found that Nitinol wire has a mode of failure due to bending and compression that is not found in other materials such as austenitic stainless steel.

SUMMARY OF EMBODIMENTS

In accordance with one embodiment of the invention, a femoral stem hip implant for insertion into a surgically created aperture in a femur includes a monolithic femoral stem made of shape memory material. The stem is configured to be inserted into the aperture and have a proximal portion and a longitudinal axis. The shape memory material within the proximal portion has a cross-section perpendicular to the longitudinal axis. At least a portion of the shape memory material within the proximal portion is in a compressed state by application of a plurality of compressive forces at a temperature below an austenitic finish temperature of the shape memory material so that the cross-section of the shape memory material expands through shape memory effect via the formation of austenite in response to a temperature increase after insertion into the aperture thereby causing a locking-force to be exerted against an inner surface of the aperture. The locking force is sufficient to stabilize the implant in the aperture.

In accordance with another embodiment of the invention, a femoral stem hip implant for insertion into a surgically created aperture in a femur includes a monolithic femoral stem made of shape memory material. The stem is configured to be inserted into the aperture and have a proximal portion and a longitudinal axis. The shape memory material within the proximal portion has a cross-section perpendicular to the longitudinal axis. At least a portion of the shape memory material within the proximal portion is in a compressed state by application of a plurality of compressive forces at a temperature below an austenitic finish temperature of the shape memory material so that the cross-section of the shape memory material expands through shape memory effect via the formation of austenite in response to a temperature increase after insertion into the aperture thereby causing a locking-force to be exerted against an inner surface of the aperture. The locking force is sufficient to stabilize the implant in the aperture. The implant further includes a connection feature integral to the stem and configured to connect to an acetabular ball.

In accordance with another embodiment of the invention, a femoral stem hip implant for insertion into a surgically created aperture in a femur includes a non-sleeved femoral stem made of shape memory material. The stem is configured to be inserted into the aperture and have a proximal portion and a longitudinal axis. The shape memory material within the proximal portion has a cross-section perpendicular to the longitudinal axis. At least a portion of the shape memory material within the proximal portion is in a compressed state by application of a plurality of compressive forces at a temperature below an austenitic finish temperature of the shape memory material so that the cross-section of the shape memory material expands through shape memory effect via the formation of austenite in response to a temperature increase after insertion into the aperture thereby causing a locking-force to be exerted against an inner surface of the aperture. The locking force is sufficient to stabilize the implant in the aperture.

In some embodiments, the portion of the shape memory material within the proximal portion may be in the compressed state by the application of compressive forces and tensile forces. The compressive forces may be applied by at least one of a forging process and a pressing process. The shape memory material may be in the compressed state such that a varying radial expansion along the length of the shape memory material results in response to the temperature increase. The shape memory material in the proximal portion may be in the compressed state such that a varying radial expansion in the proximal portion results in response to the temperature increase. The stem has a distal portion and the shape memory material within the distal portion may be in an untrained state. The stem has a distal portion and the shape memory material within the distal portion may be in the compressed state. The shape memory material may be in the compressed state such that the proximal portion radially expands by a different amount than the distal portion in response to the temperature increase. At least 70% of the cross-section may be occupied by shape memory material or the entirety of the cross-section may be occupied by shape memory material. The implant may include at least one of a porous surface coating, a drug coating, and a collagen coating The hip implant may include at least one of a textured surface and a porous surface. The shape memory material may be Nitinol, and/or a titanium-niobium alloy. The stem may have a distal portion having two or more branches.

BRIEF DESCRIPTION OF THE DRAWINGS

The foregoing features of the invention will be more readily understood by reference to the following detailed description, taken with reference to the accompanying drawings, in which:

FIG. 4 depicts a prosthesis that is decorated with projections;

FIG. 5 depicts a prosthesis with a flexible stem in accordance with an embodiment of the invention;

FIG. 11 shows a finite element model of the prosthesis of FIG. 1a.

DESCRIPTION OF ILLUSTRATIVE EMBODIMENTS

Illustrative embodiments of the present invention include prostheses for use in arthroplasty. By way of explanation, examples are given of femoral prosthetics, but the invention also pertains to other long-bone prosthetics, including those used for implantation in a humerus, tibia, fibula, radius, or ulna. Unless noted otherwise, the prostheses described herein include an expanding shape-memory portion that exerts an active locking force upon a proximal bone region due to a shape-memory transition. As a result, a patient with the prosthesis may enjoy a shortened recovery due to increased primary stability. The locking force may also exclude wear particles from the prosthesis-bone junction, and may induce an increase in bone density in the proximal bone, thereby improving the long-term stability of the implant, and perhaps extending the use of cementless implants to include additional patient populations.

Furthermore, embodiments of the present invention prevent stress-shielding by allowing for increased diaphyseal flexibility through the use of a stemless design or a flexible distal shaft portion. In embodiments, a majority of the bone-locking force (e.g., at least 70% of, at least 90% of, or substantially all) is applied to region of the bone that is no more distal than the metaphysis, no more distal than the lesser trochanter, or to the region of the calcar femorale.

Figure 1A:
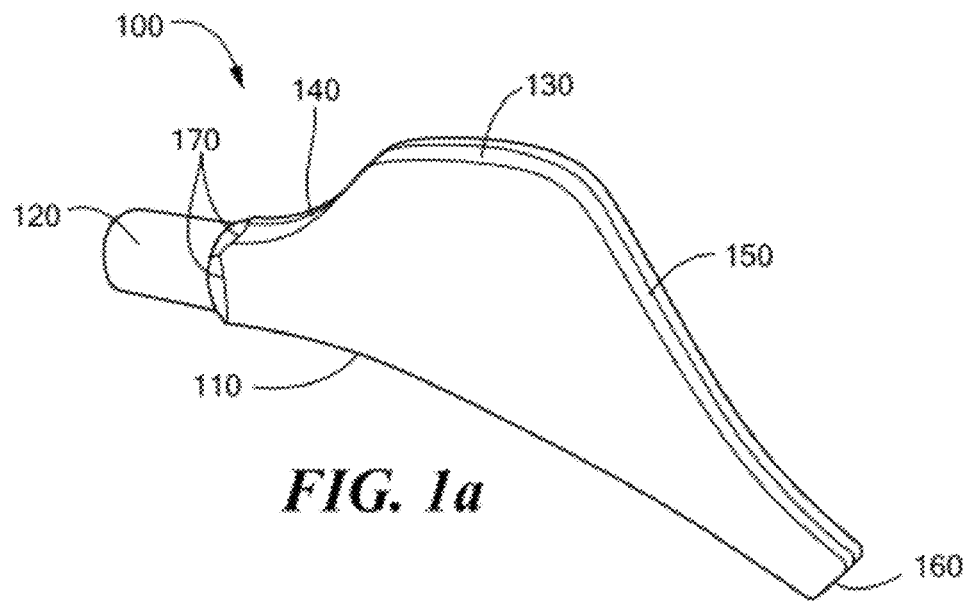
FIG. 1a depicts a prosthesis in accordance with an embodiment of the present invention.

FIG. 1a shows a prosthesis 100 in accordance with an illustrative embodiment of the present invention. The prosthesis 100 includes a body 110 (also referred to as a "shaft") that is inserted into a resected long bone of a patient. The body 110 is structured to transfer a load produced by the weight of a patient to a femur of the patient. A neck 120 acts as a connection feature for connection to a ball (not shown) that is suitable for insertion into an acetabulum of the patient or prosthetic acetabular cup.

The body 110 is constructed, in whole or in part, from a shape memory material. For example, the body may be entirely constructed of a shape memory alloy such as Nitinol. Alternately, the body 110 includes a coating of shape memory material fused to a solid core. The body may 110 also be hollow or porous with sufficient material remaining present to bear the weight of the patient. In an embodiment, a majority of the body 110 may be entirely composed of a shape memory material as measured in a cross section taken orthogonally to an axis defined by the bone in which it is implanted. Alternately, the cross-section may be characterized by a majority of shape-memory material or at least 70% shape-memory material. In addition to Nitinol, other suitable shape-memory material may be used, including Ti—Nb alloys, suitably robust shape-memory plastics, composite materials, and materials produced using nanotechnology, which may be increasingly discovered as that art progresses.

As discussed below, the shape memory material provides an active bone-locking force, the majority of which is at or above (i.e., proximal to) the level of the metaphysis. The locking force actively applies an outwardly directed force upon a bone in which it is inserted and thereby increases primary stability (i.e., stability that is not a result of bone-ingrowth). Thus, the bone-locking force of the prosthesis 100 differs from the contributions to long-term stability caused by bone-ingrowth. However, the body 110 or other portions of the prosthesis may include features, such as textured or porous surfaces, that are designed to promote osseointegration for additional long-term stability.

The shape-memory material is integral to the bone-locking portion and changes shape in response to a temperature change. In various embodiments, the shape memory material may utilize one or more of a 1-way shape memory effect, and a 2-way shape memory effect. Nitinol and other shape memory alloys may be more flexibly that conventional alloys used in long-bone prosthetics. Additionally, to increase flexibility, a pseudoelastic shape-memory material may be used for portion of the body 110. The flexibility of the body 110 may allow a recoverable strain similar to that of a normal bone. According to embodiments, the shape-memory effect need not be the maximal expansion achievable for a given material. In contrast, the shape-memory material may be prepared in a manner that causes it to expand by a predetermined sub-maximal amount in the absence of a bone. Accordingly, when implanted into a resected femur, the so-prepared shape memory material will apply a corresponding force, which may be less than the maximal force achievable for a shape-memory bone-locking region of a given size. For example, while Nitinol may be used to achieve as much as an 8% shape change, a Nitinol body may prepared in a manner that causes it to expand by less than 8% or, more preferably, less than 5% or less than 1%. The degree of force applied may be optimized to balance short-term and long-term stability of the prosthesis by applying sufficient force to give suitable initial stability while avoiding either over-compression of the bone and associated pressure-induced necrosis or bone-fracture.

Figure 1B:
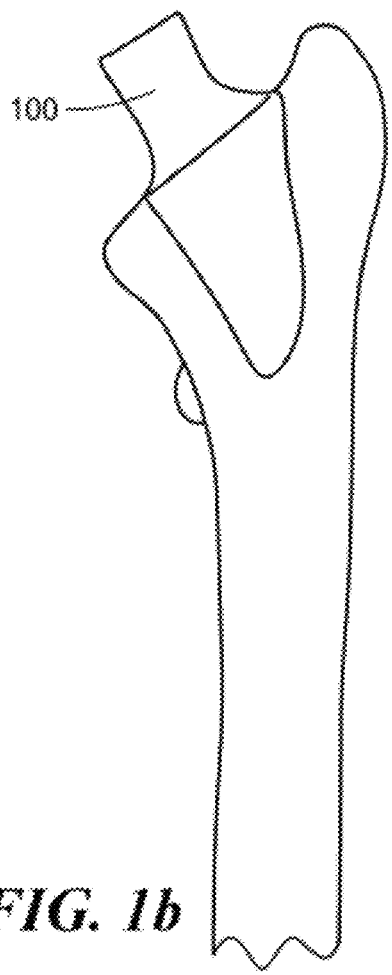
FIG. 1b schematically shows a prosthesis of FIG. 1a implanted in a bone in accordance with an alternate embodiment of the invention.

The prosthesis 100 includes several optional features. A lateral flare 130 of body 110 may help stabilize the prosthesis in the bone by using a high femoral neck cut and "round-the-bend" insertion technique as is known in the art in conjunction with the Proxima™ line of femoral prosthetics (DePuy, Leeds, UK). The lateral flare may have a proximal section 140 and a distal section 150. However, in an alternate embodiment shown in FIG. 1b, the lateral flare 130 is omitted; a design change for which the bone-locking expansion of the body 110 may compensate by providing offsetting or comparable short-term stability. In the embodiment of either FIG. 1a or 1b, a short stem 160 may be included, and may be flat, rounded, tapered or pointed. The stem 160 of the present invention allows the flexibility of the femoral diaphysis to be maintained in order to increase the long-term stability of the implantation. Flexibility may be maintained by using a short stem 160 that does not extend into the diaphysis of the bone. Alternately, only a minority of the stem length may extend into the diaphysis. In embodiments described below, the stem does extend into the diaphysis to improve short-term stability, but is flexible. As is known in the art, the prosthesis may be sterilized prior to use. As discussed in more detail below, the prosthesis 100 may also include anti-rotation features such as facets 170.

Figure 2:
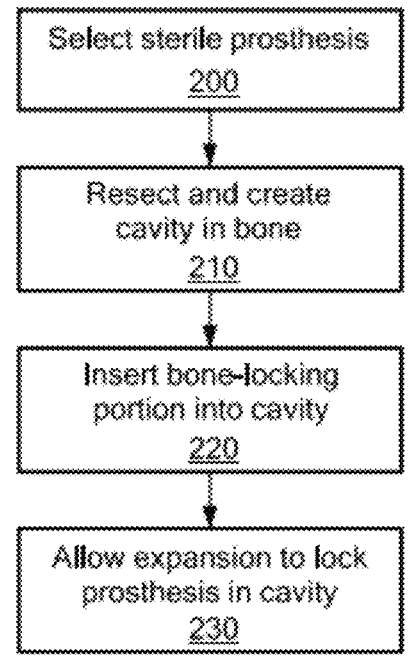
FIG. 2 depicts a flow diagram for a method of performing an arthroplasty in accordance with an embodiment of the present invention.

FIG. 2 shows a flow diagram for a method of implantation in accordance with an embodiment of the invention. First, a sterile prosthesis is selected in a size that is appropriate for the patient (step 200). The prosthesis is at a temperature below its transition temperature (e.g., chilled by refrigeration or storage on ice, or at room temperature with a transition temperature that is between room temperature and body temperature). Selection of the prosthesis may be aided by using a stencil on an x-ray, or using computer-guided techniques. The prosthesis may be a standard size, or custom-made for a particular patient. In any case, the prosthesis may be chosen to provide adequate stability, without damaging the bone during implantation.

The bone is resected and an aperture (i.e., a cavity) is surgically created in the bone using reamers and broaches, as is known in the art (step 210). The body 110, which includes the bone-locking portion in its compressed state, is inserted into the aperture so that the bone-locking portion is situated in the metaphysis (step 220). Typically, a broach or other tool may be used that is calibrated for use with a particular prosthesis to give a desired fit. As a result, a bone-to-prosthesis gap of an approximately predetermined size is created at the junction of the aperture and prosthetic surface. In an embodiment, when implanted into an average-sized patient, the body 110 will extend by less than or equal to 5 inches into the aperture.

As the bone-locking portion of the body 110 approaches or surpasses its transition temperature, a martensite to austenite transition of the shape-memory material becomes thermodynamically favored. As a result, the bone-locking portion will radially expand, filling the gap left at the junction. Additionally, the bone-locking portion may possess a potential for further radial expansion, were it to be hypothetically unconstrained by bone. Accordingly, the bone-locking portion exerts a radially outward bone-locking force upon the bone at the junction. As a result of the application of bone-locking force, the prosthesis 100 is more securely lodged in the aperture than a conventional prosthesis made without the use of shape-memory material (step 230). In accordance with an embodiment of the invention, the prosthesis 100 is inserted into the aperture and its position adjusted prior to full locking expansion. If the prosthesis is capable of 2-way shape-memory or stress-induced martensite behavior, as discussed below with reference to FIG. 6, the prosthesis 100 may be cooled to return it to a contracted form in order to unlock it for purposes of repositioning or removal and replacement.

According to an embodiment, the shape-memory alloy bone-locking portion, which may be the entire prosthesis 100, expands throughout its volume to apply outwardly radial locking-force to thereby seal the junction between the prosthesis 100 and the bone. To enhance, the seal, a sealing portion of the body 110 (e.g., a proximal portion or the entire body) may be substantially uninterrupted; e.g., with no grooves, holes or other substantial discontinuities in its exterior surface.

The bone-locking force may increase primary stability (i.e., the initial stability immediately after implantation) to thereby reduce patient recovery times and allow greater weight-bearing during patient recovery. In various embodiments, the bone-locking force may provide the majority of, at least 70% of, or substantially all of the forces contributing to primary stability. The bone-locking force may also increase long-term stability (e.g., to 50 years or more). Without wanting to be bound by the scientific explanation, long-term stability may be increased by promoting elevated bone density and osseointegration in the vicinity of the bone-prosthesis interface based on the ability of bone to remodel in response to the radially applied stresses. The ability to increase bone density may be useful to patients with low bone density; e.g. those with osteoporosis. Accordingly, the prosthesis may be used with or without cement according to the circumstances. Moreover, because the bone-locking force is applied in the proximal regions of the bone, there is little or substantially no stress-shielding due to subtrochantric or other distal buttressing. For example, the majority of, at least 70% of, at least 90% of, or substantially all of the force may be applied to regions no more distal than the trochanter minor (lesser trochanter), at or above the level of the metaphysis, at the epiphysis, or in the vicinity of the calcar femorale. Furthermore, the bone-locking force may act to sealingly exclude wear debris or other particles from entering the junction and avoid corresponding adverse effects. Additionally, the bone-locking force may reduce cyclic micromotions of the prosthesis 100 relative to the bone in which it is implanted. Such micromotions may be associated with long term instability of a reconstructed bone.

Another advantage of using an expanding bone-locking portion is that with such a device, it is not necessary to use a tight interference fit between the prosthesis and the aperture, and accompanying insertion by hammering, as is common with conventional cementless prostheses. Accordingly, a larger gap may be used (e.g., a 0.5 to 5 mm gap). Expansion of the prosthesis may be selected to apply a desired bone-locking force for a given gap size. Increasing the gap size may militate for using a prosthesis capable of a greater degree of expansion. By preventing scraping associated with forcible insertion of a prosthesis in an aperture, increasing the initial gap size may prevent damage to the bone and avoid the creation of wear particles. Additionally, by eliminating the need for hammering, or if hammering is used, by reducing the required force, use of the prosthesis 100 reduced the chance of fracturing the bone. Nonetheless, in some instances, it may be desirable to use only a small gap to aid in aligning and maintaining the alignment of the implant prior to the expansion and corresponding application of locking force. The prosthesis may be held in its correct orientation within the bone during the expansion process until the expansion has proceeded to a degree sufficient to stabilize the prosthesis within the bone. The temperature change may occur through warming of the prosthesis due to heat from the body of the patient or external heaters may be used to accelerate the process.

In addition, an increased gap allows for the prosthesis to optionally be surrounded by a gap-filling material that bridges the junction between the prosthesis and the bone. Optionally, the gap-filling material may be strongly or loosely attached to the prosthesis. The gap-filling material may include a variety of materials including a membrane, gel, fibrous or woven mesh, foam, or a plastic or metal sleeve. The gap-filling material may be applied to the prosthesis prior to insertion into the aperture, or, alternately, injected directly into the gap. As discussed below, the gap-filling material may be a metal foam, collagen, or other suitable material.

The gap-filling material may play a variety of functions. The gap-filling material may improve the seal formed at the junction to thereby exclude particles. For this purpose, a deformable, gel, paste or collar may be used. The deformable material may include or consist of collagen (e.g., a collagen membrane). Similar materials may be used to improve the fit and stability of the implant. If cement is to be used in the procedure, the cement may act as a gap-filling material. The gap-filling material may act as a scaffold for bone growth. The gap-filling material may include substances that encourage bone growth. For example, the gap-filling material may include a peptide hydrogel (e.g., Puramatrix™, 3DM Inc.). The gap-filling material may also include growth factors such as peptide growth factors that are known in the art to enhance bone growth. The gap-filling material may include an antimicrobial or antifungal substance (e.g., small molecule antibiotics or colloidal silver). The various biologically active substances mentioned, or others, may be released from a gap-filling matrix material in a time-released manner.

In accordance with illustrative embodiments, an implant formed from shape memory alloy has a drug (e.g., a small or large molecule antibiotic, anti-inflammatory, or growth factor) applied to it either internally and/or externally. Specifically, in illustrative embodiments, a drug coated, self-expanding implant should not scrape or interfere with the bone during insertion, keeping the coated surface intact (if the surface is coated). The implant will then radially expand to contact the femoral bone, which will locally deploy the antibiotics in the proper place against the bone tissue. The processes used to apply the drug or drug/polymer solutions to the prosthesis 100 can be based on one of the following methods (among others): dipping, ultrasonic spray coating, painting (air brush), ink jet coating, and deposition along the stem using syringes. Some techniques combine one of the deposition methods above with a continuous stem rotation to eliminate the excess fluid. The drug and polymer solutions can be deposited very precisely (location and amount) onto the surface of body 110. Complex coatings using multiple different drugs or drug concentrations, or different polymers deposited onto the prosthesis 100, will prevent the coating from scraping off during insertion into the bone. Drug coatings may also be applied to a porous surface of the prosthesis.

Figure 3:
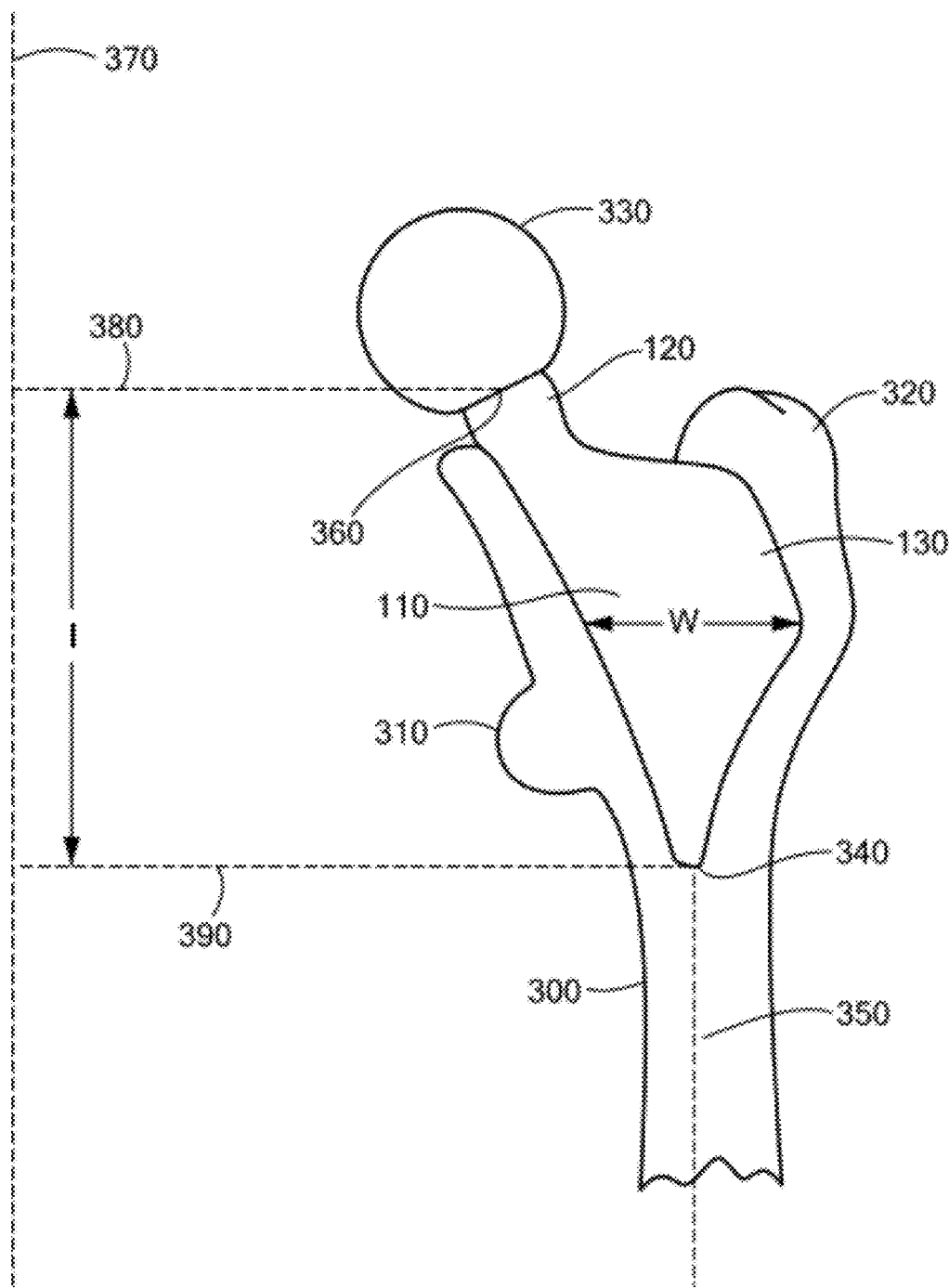
FIG. 3 schematically shows the prosthesis of FIG. 1a implanted in a bone.

FIG. 3 shows an embodiment of the present invention, in which a Nitinol prosthesis 100 is embedded in a femur 300. The body 110 is wedged in the proximal (epiphyiseal/metaphyseal) bone such that the majority of the prosthesis is located at or above the lesser trochanter 310. An optional lateral flare is wedged by the greater trochanter 320. A ball 330 is attached to the neck 120. The distal-most tip 340 of the body 110 extends to the proximal portion of the medullary canal. In this embodiment, the distance from the tip 340 to a neck junction 360 between the ball 330 and the neck 120 is designated as the length of the prosthesis. The length may be, for example, less than or equal to 5 inches.

In order to provide diaphyseal flexibility and proximal locking, in an embodiment, the length/width ratio of the prosthesis is less than or equal to 5. In a preferred embodiment, the length/width ratio is less than or equal to 4. In the embodiment, of FIG. 1a, the length/width ratio is about equal to 3. The length/width ratio is defined by implanting the prosthesis into a resected bone or suitable model thereof (e.g., an animal bone or reamed plaster cast of a bone). The length (l) is defined as the distance from a projection line 380 drawn from the centroid of a plane defined by the neck junction 360 to a line 370 parallel to an axis defined by the shaft of the femur 300 to a second projection line 390 drawn from the tip 340 to the line 370. The width (w) is defined as the longest line that can be drawn that is perpendicular the axis of the shaft.

In addition to the proximal bone-locking action of the shape memory material, additional features may be included to enhance long-term stability. For example, as shown in FIG. 4, the body 110 may be decorated by protrusions 400 such as barbs, teeth, tangs or flutes, which may also be constructed from shape memory material and trained to lockingly expand upon elevation of the temperature. Additionally, the body 110 may include a textured surface, which may be constructed from fused beads, wire mesh, porous hydroxyapetite, or grooves and ribs. The textured surface may be applied by vapor deposition or sintering.

The protrusions 400 may assist in preventing rotation of the prosthesis 100 within the aperture. Additional features and methods may be included to disfavor detrimental rotation of the prosthesis 100. The prosthesis may be eccentric (i.e., deviating from cylindrical, conical or frustoconical). In a specific eccentric embodiment, the proximal portion of the body 110 may include facets 170 (as shown in FIG. 1a). The eccentricity could also be characterized by an oval or cloverleaf cross section. In use, a correspondingly eccentric bore is created in the bone 300, and the prosthesis is inserted. After warming and expansion, and because shape-memory material is used in the proximal portion of the body 110, the prosthesis 100 will be locked in a manner that is resistant to torsional displacement. For example, 6 facets 170 may be used and a complementary (hexagonal) proximal aperture created. Protrusions 400 may compensate for a prosthesis 100 that is somewhat round in cross-section; e.g., the prosthesis 100 shown in FIG. 1b.

The proximal portion of the body 110 may also include a bottle-bore shape; i.e., having a taper so that the portion adjoining the neck is narrower than the immediately distal portion. When a corresponding proximal aperture is used, the proximal body will expand to create an implantation that is resistant to proximally-directed dislodgement. The opposite configuration may also be used—the most proximal body portion may be wider than the immediately distal portion and a corresponding cavity created in the proximal aperture. Accordingly, the resulting implantation will resist distally-directed dislodgement. In addition, both of these effects may be combined as with a threaded arrangement or series of circumferential ribs in the proximal body 110 and corresponding grooves created in the proximal bone aperture.

As mentioned above, the body 110 is designed to permit flexure of the bone shaft and this may be accomplished by use of a shortened or stemless prosthesis, which, by not extending significantly into the diaphysis, may avoid the stiffening of the diaphysis associated with stemmed prostheses. A body 110 that is predominantly constructed from a shape memory alloy will have a high degree of flexibility. For example, Nitinol has an elastic modulus of 48 GPa and Ti-26Nb has an elastic modulus of 80 GPa, whereas Co—Cr—Mo, 316-L stainless steel and Ti-gAl-4V have elastic moduli of 230, 200 and 110, respectively. Thus, the shape memory alloys Nitinol and Ti-26Nb have an elastic moduls that is closer to the elastic modulus of cortical bone (15 GPa) than conventional prosthetic materials. A more flexible prosthesis will reduce the load-sharing ratio between the prosthesis and the bone in which it is implanted and will minimize stress-shielding accordingly. A closer matching of elasticity between the prosthesis and bone may also reduce interfacial shear stresses.

Optionally, the prosthesis 100 may expand by a first amount in a first region and by a second amount in a second region. For example, FIG. 5 shows an illustrative embodiment in which a proximally locking short or stemless body is connected to an elongated flexible shaft 500. The flexible shaft 500 may be composed of a material that is flexible, and may be composed of a material that is as flexible or more flexible than stainless steel. The flexible shaft 500 may also include pores, a roughened surface, a bioactive coating, or other features designed to promote ingrowth to enhance long-term stability of the prosthesis. In an embodiment, the flexible shaft 500 is composed of pseudoelastic Nitinol or martensitic Nitinol (which may be unworked). The stem may also be composed of Nitinol that has been trained to expand to a lesser degree (including not at all) than the programmed expansion of body 110. In another embodiment, the flexible shaft 500 is split into 2 or more branches with a central gap to permit bending of the branches in response to applied bending moments. The branches may be composed of a shape memory alloy or other material.

In accordance with an embodiment of the invention, the elastic modulus varies along the proximal-distal axis of the implant. This may be accomplished by selectively training a shape-memory alloy. The proximal portion of the implant may be trained to expand at body temperature and contract at another temperature so as to secure the implant through application of force to the proximal portion of a bone. In contrast, the distal portion of the implant may be untrained or trained in a different manner so as to create a lower elastic modulus in the distal portion. In a specific embodiment, Nitinol is used as the shape-memory alloy and is trained to expand in the proximal portion of a stem, and untrained in the distal portion; the untrained Nitinol is in its martensitic state and is more flexible than the trained austenitic Nitinol.

If the expansion of the body 110 in response to a temperature shift causes elongation of the body 110, the tip of the prosthesis may expand in a manner that compresses the bone marrow. Accordingly, it may be desirable to remove a portion of the marrow immediately below the distal extent of the prosthetic. This gap may be filled with a gap-filling material, which may be a resilient material and/or one of the materials mentioned above with respect to the filling of the prosthesis-bone junction.

The prosthesis 100 may also be modular, meaning that the shape-memory proximal portion may be assembled with other portions in order to give a better fit for a given patient. For example, a proximal locking portion may be assembled with a stem, neck, and ball. In an embodiment, the body 110 is made from nitinol, and the neck is made from another alloy that is more resistant to bending-induced fracture.

Figure 6:
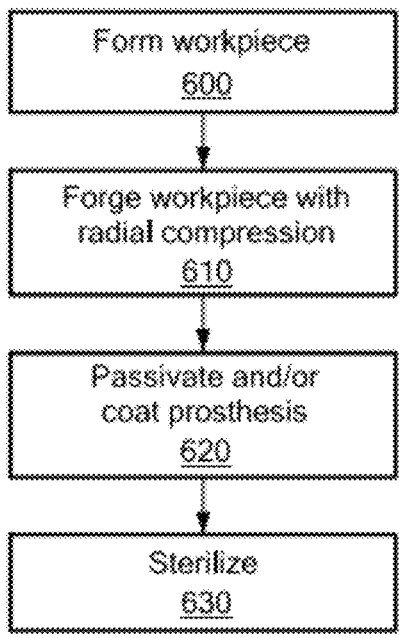
FIG. 6 depicts a flow diagram for a method of manufacturing a prosthesis in accordance with an embodiment of the present invention.

In accordance with an embodiment of the invention, FIG. 6 shows a flow diagram for a method of manufacturing a proximally self-locking prosthesis. A Nitinol workpiece (e.g., a billet) is selected. The Nitinol material may be selected to have an austenite finish temperature ($A_f$) that is at or below body temperature (about 37° C. for a human) so that the resulting prosthesis 100 will be in an expanded form after implantation. For example, the prosthesis 100 may have an $A_f$ of 30° C. The prosthesis 100 is formed to net shape at a temperature above $A_f$, i.e., to the final expanded shape after expansion (step 600). The forming step 600 may include one or more of machining, forging, casting, sintering or hot-isostatic-pressing.

The formed implant is then "trained" using a thermo-mechanical treatment regime (step 610). Training may be commenced by heat treating the prosthesis and then cooling in order to establish the martensitic state. The training generally includes straining the material to altering the shape at a lowered temperature. In an embodiment, the compression includes forging in a manner that applies compressive forces having at least a component that is orthogonal to a central axis of the prosthesis 100 (e.g. an axis drawn from the tip 160 to the centroid of the neck 120, or an axis corresponding to the axis of a bone in which the prosthesis 100 will be implanted). Optionally, or in addition, forces may be applied with at least a component that is orthogonal to the central axis of a bone in which it is implanted (e.g. as described with reference to FIG. 3). When performed at a temperature below $A_f$, this process is referred to as "cold-working". The forging process may include swaging or rotary swaging. Mechanical forge presses, screw presses, hydraulic presses, swage or pointer machines can be employed to train the prosthesis 100. Alternately, the prosthesis 100 may be pulled (i.e., tensioned on a 2-column tensile pulling machine) longitudinally to both extend its length and decrease its width. Although the pulling process may be simpler, the forging process may allow for a greater degree of control in the compression. For example, certain regions of the prosthesis may be selectively compressed or compressed to varying degrees. In an embodiment, the prosthesis 100 is forged to generate varying compression along its length. For example, because untrained Nitinol is generally more flexible than trained Nitinol, differential training may be used to provide proximal locking while maintaining greater distal flexibility in a stemmed or stemless prosthesis 100. Multiple discreet locking regions may also be formed by machining raised zones (e.g., patches, ridges, or bumps) and then compressing those zones. A combination of forging and pulling steps may also be used to train the prosthesis 100. The use of forging may enable the creation of short or stemless shape-memory prosthesis 100 and allow for the creation of complex shapes such as the later-flare design of FIG. 1a.

For two-way shape-memory effect (SME) training, the prosthesis 100 may be cooled to below the martensite finish temperature (Mf) of the material and deformed to the desired shape. It is then heated to a temperature above $A_f$ and allowed freedom to take its austenitic shape. The procedure is repeated (e.g., 20-30 times). The prosthesis 100 now assumes its programmed compressed shape upon cooling to below $M_f$ and to the expanded shape when heated to above $A_f$.

Alternately, stress induced martensite (SIM) training may be employed. For SIM training, the prosthesis 100 is deformed to a compressed shape just above its martensite start temperature ($M_s$) to generate stress-induced martensite and then cooled to below its $M_f$ (martensite finish temperature). Upon subsequent heating above $A_f$, the prosthesis 100 takes its original austenitic shape. This procedure is repeated (e.g., 20-30 times). Alternately, other metallurgical techniques that are known in the art to produce 2-way SME may be employed.

The expansion of a 2-way shape memory alloy component differs from the thermal expansion that may occur in a conventional alloy in at least the following ways: (i) SME components exhibit martensite to austenite transformations at a crystal level, (ii) SME components may be trained to either expand or contract, (iii) the percentage shape change due to thermal expansion is usually −0.001% per ° C., while the shape change due to SME can be as much as two orders of magnitude greater; (iv) the temperature ranges at which a shape-memory alloy exhibits a SME can be adjusted by thermo-mechanical treatment; (v) the SME material may exhibit a hysteresis in its temperature/displacement profile; (vi) the SME material may exhibit hyperbolic temperature/displacement behavior.

A 1-way shape-memory effect bone-locking portion may be employed. The 1-way SME material will decompress and expand upon heating, but will not regain its original shape upon subsequent cooling. Thus, a 1-way SME prosthesis 100 should be kept at low temperature and/or mechanically constrained prior to use. The 1-way SME material may be Nitinol that has been compressed only once in training. The use of 1-way SME may be advantageous in terms of preventing long-term material fatigue-failure that may occur due to repetitive austenite to martensite transitions that may be induced by the repeated stresses applied during use.

In a specific illustrative embodiment, the process includes hot-forging the prosthesis 100 to near net shape at a temperature above $A_f$, finish-machining the forged piece to net shape, and training the prosthesis 100 at lower temperature (e.g., below $A_f$) to radially compress the prosthesis 100 by less than 8%, or, more preferably, less than 5% or less than 1%.

After training (step 610), the prosthesis 100 may be passivated and/or coated to provide a protective layer in order to discourage corrosion, improve biocompatibility, to promote osseointegration, or a combination of the foregoing. Passivation may include prolonged exposure to elevated temperature in the presence of oxygen in order to build a metal oxide layer. A metal foam or other porous metal material, of about 2 mm thickness for example, may serve to promote osseointegration and as a gap-filling material to improve the proximal seal by deforming radially and circumferentially to fill the gap and any deformities in the aperture. The porous metal material described in U.S. Pat. No. 6,063,443 and that commercialized as Trabecular Metal™ (Zimmer, Inc.) may be a suitable porous metal material. The porous material may also be porous Nitinol. An explanation of sterilization and surface treatments may be found in Shabalovskaya, S., "Surface, corrosion and biocompatibility aspects of Nitinol as an implant material", Bio-Medical Materials and Engineering 12 (2002) 69-109 69. Sterilization (step 630) may be accomplished through a variety of means including steam, heat, ethylene oxide, plasma, electron or gamma irradiation. Surface coating may include the application of a porous coating including a metal foam, such as titanium foam.

Figure 7:
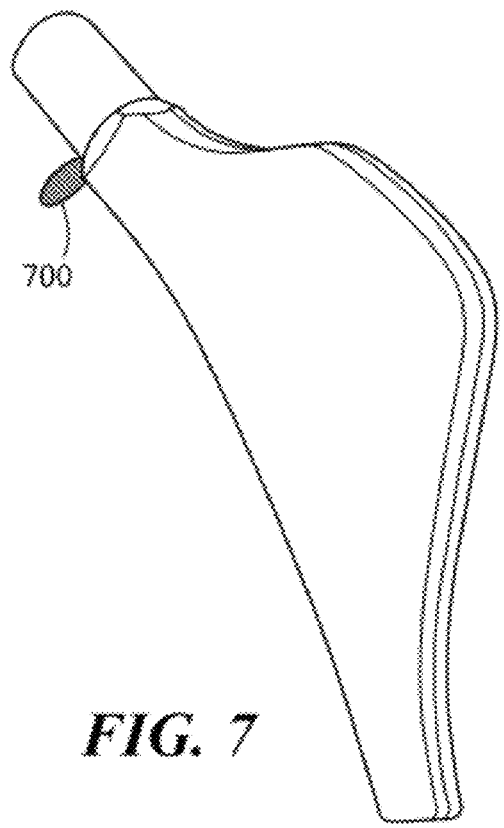
FIG. 7 depicts a prosthesis with a lateral projection in accordance with an embodiment of the present invention.
Figure 8:
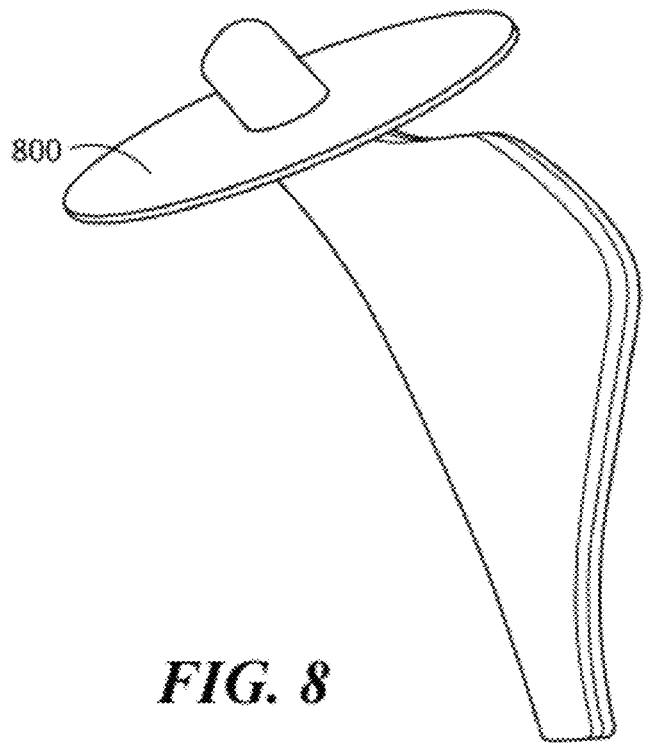
FIG. 8 depicts a prosthesis with a proximal skirt in accordance with an embodiment of the present invention.

In accordance with an embodiment, the prosthesis 100 includes one or more radially extending features that are structured to sit above the femoral cut. FIG. 7 shows a prosthesis 100 with a lateral projection 700 that is positioned to sit proximal to the femoral cut after implantation and to provide additional safeguarding against unwanted distal displacement of the prosthesis in the aperture. FIG. 8 shows a prosthesis 100 with a proximal skirt 800. The skirt 800 may be made of shape-memory material. Optionally, the skirt 800 may be shape memory material and may be trained to curve distally upon elevation of temperature and shifting to its austenitic state, thereby surrounding the proximal portion of the bone and preventing acetabular wear particles from entering the prosthesis-bone junction. Alternately, conventional material such as stainless steel or other biocompatible alloy may be used in a statically curved or flat configuration.

In accordance with an embodiment of the invention, a prosthetic 100 includes a Nitinol body 110 of sufficiently short length to avoid bending-induced fracture over the lifetime of a prosthetic or of a patient. By confining the Nitinol portion primarily or entirely to regions at or above the metaphysis, bending-induced fracture of the prosthesis is avoided due to the absence of a long stem with a bending moment. As discussed below, computer modeling of a short-stemmed prosthesis 100 indicates sufficient robustness of the short-stemmed design when exposed to cyclic compressive forces simulating use in a patient having a prosthesis implanted in the proximal bone.

In an embodiment, the bone-locking region creates a bone-locking force that creates a sufficient primary stability so that a 2.5 kN force applied to the prosthesis causes a micromovement of the implant relative to the bone of no more than 50 microns.

In accordance with an embodiment, the prosthesis 100 does not fracture during application of an endurance test. The endurance test may be conducted according to ISO 7206-4 (including the 1995 and 2002 standards) and may include embedding the prosthesis in an embedding medium and applying 5,000,000 cycles of application of a cyclic load of 2 kN with a minimum load of 300N and a maximum load of 2.3 kN. The embedding medium is a casting medium that will not crack or break under the load applied during testing, and will not exhibit excessive deformation or creep, and is reproducible in strength and other characteristics, and has a modulus of elasticity between 3 GPa and 6 GPa. The prosthesis 100 may be constructed of Nitinol and have a sufficiently short stem length to meet the ISO 7206-4 standard.

Example 1

Finite Element Modeling of a Long-Stemmed Implant

A computational model of a long-stemmed Nitinol prosthesis was created using finite element modeling techniques. The results warn that long-stemmed prosthetics with Nitinol stems may be susceptible to bending-induced fracture.

Figure 9A:
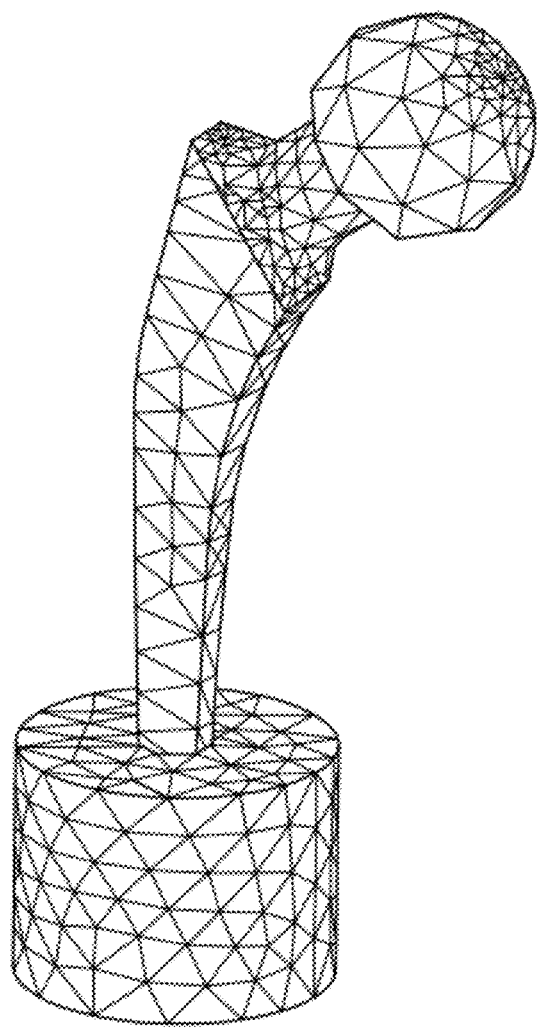
FIGS. 9a and 9b depict finite element models of a long-stemmed prosthesis.
Figure 9B:
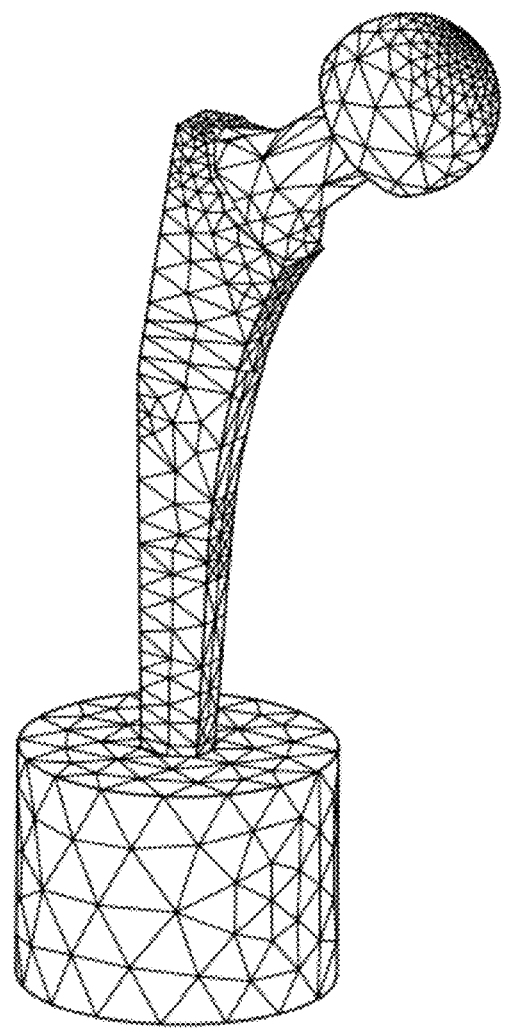

FIGS. 9a and 9b show a finite element model geometries used and designated as "Hip A" and "Hip B" respectively. The material properties for the finite element analyses were assumed to be linear elastic and isotropic. CoCrMo and Nitinol used in these analyses were assumed to follow Hooke's Law, and frictional forces could be neglected since the applied force was much higher than the frictional forces. All finite element models were assumed to be linear and uncemented. The force(s) transmitted from walking were assumed to be transmitted from the femur into the implant, where the force then was transmitted to the ball. From there, the force was then transmitted into the liner and cup. The force transmitted from the liner/ball interaction was assumed to be equal to the applied force due to the press fit between the two objects. The force applied to the hip stem was varied from 2.5 to 7.5 kN, but any force can be extrapolated from these two forces. The force was assumed to be completely transmitted from the acetabulum to the ball on the hip stem, with no losses in between. These forces were chosen because a typical gait cycle generates up to 7 times the body weight at the hip joint.

The force acting on the ball of the hip stem was varied from 2.5 to 7.5 kN. There were three different constraint conditions used: the distal end of the hip prosthesis was constrained, at and below the mid plane of the stem, and lastly at and below where the neck protrudes from the hip prosthesis.

Austenitic and martensitic Nitinol was applied to the stem and neck of hip designs. The ball of the implant was CoCr. This research was performed to determine the effects of applying Nitinol to the stem.

Figure 9C:
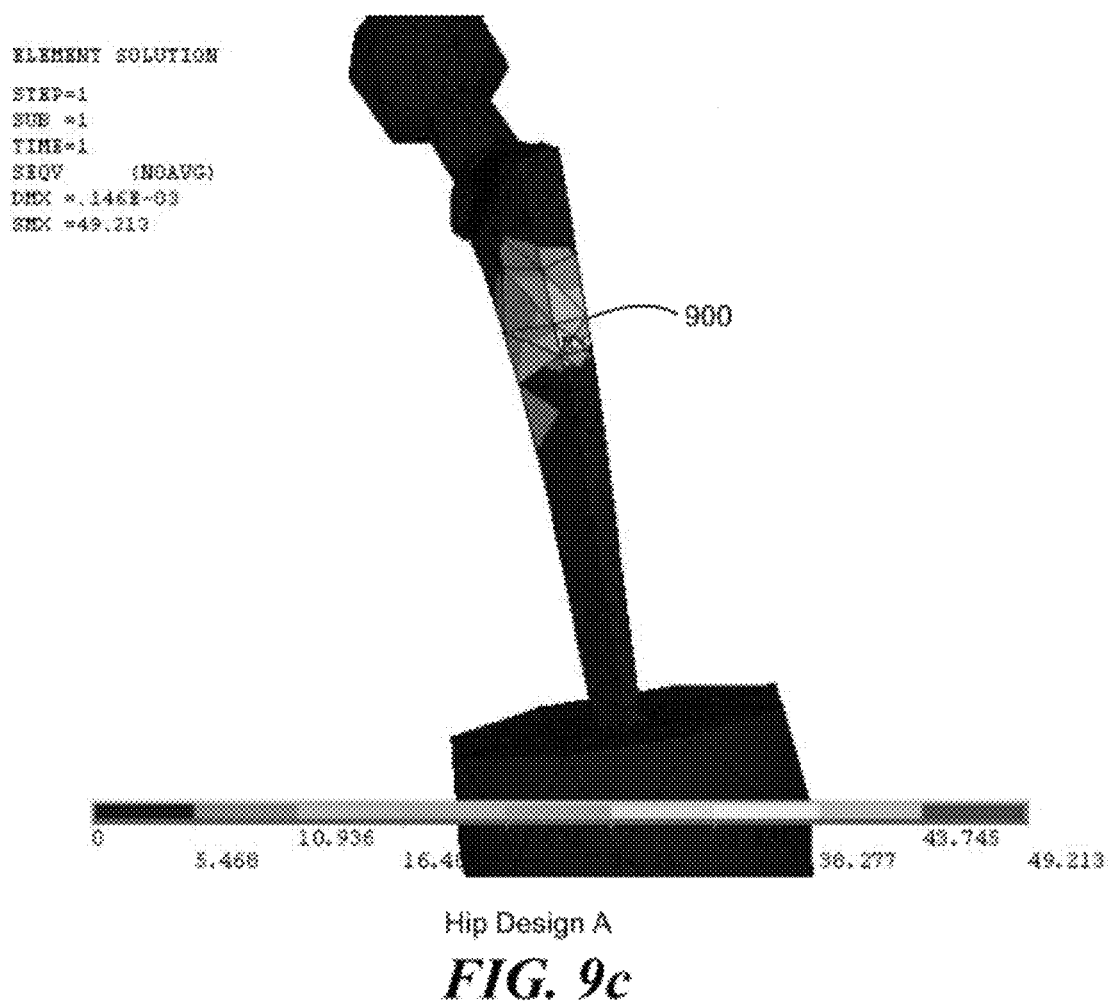
FIGS. 9c and 9d depict finite element model output corresponding to FIGS. 9a and 9b, respectively.
Figure 9D:
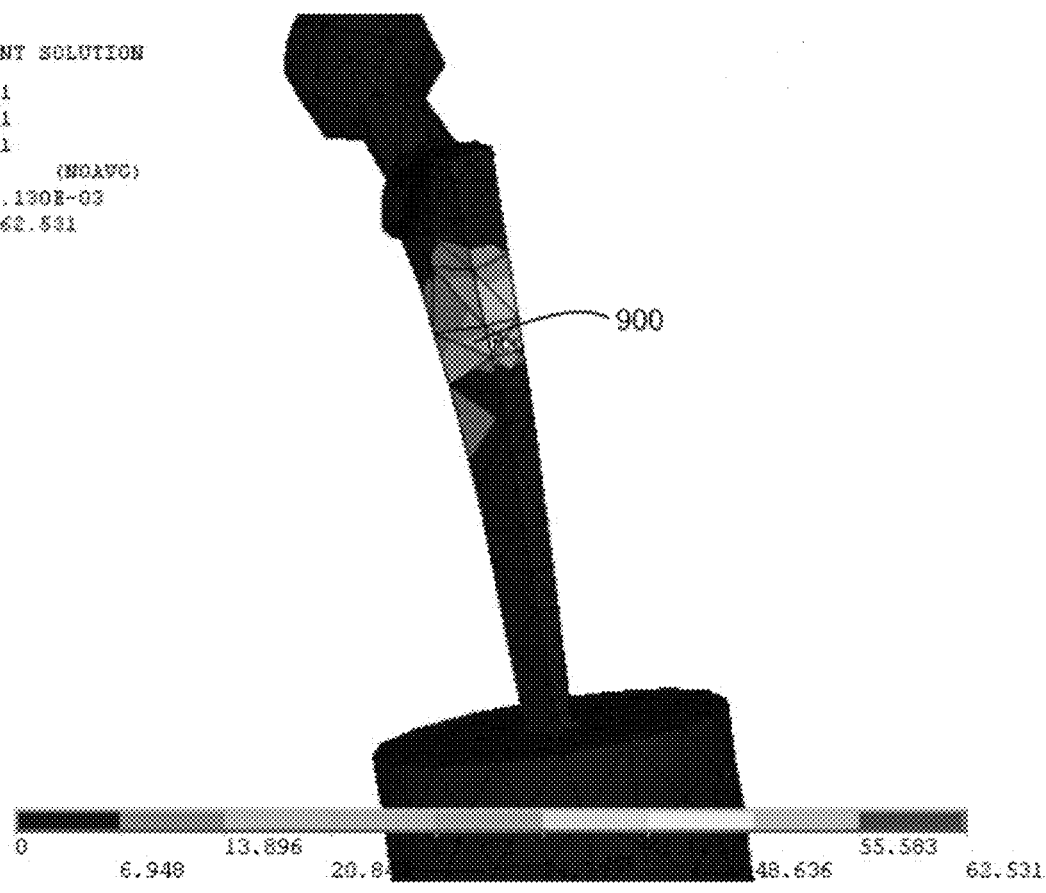

The maximum stresses 900 occur above the region of fixation, as shown in FIGS. 9c and 9d. The maximum stress 900 for the hip design B (FIGS. 9b and 9d) was 9.07 MPa when austenitic Nitinol was used, and 9.41 MPa when the martensitic Nitinol was applied. For hip A (FIGS. 9a and 9c), the maximum Von Mises stresses were 6.60 and 7.14 MPa for the austenitic and martensitic Nitinol, respectively.

Figure 10:
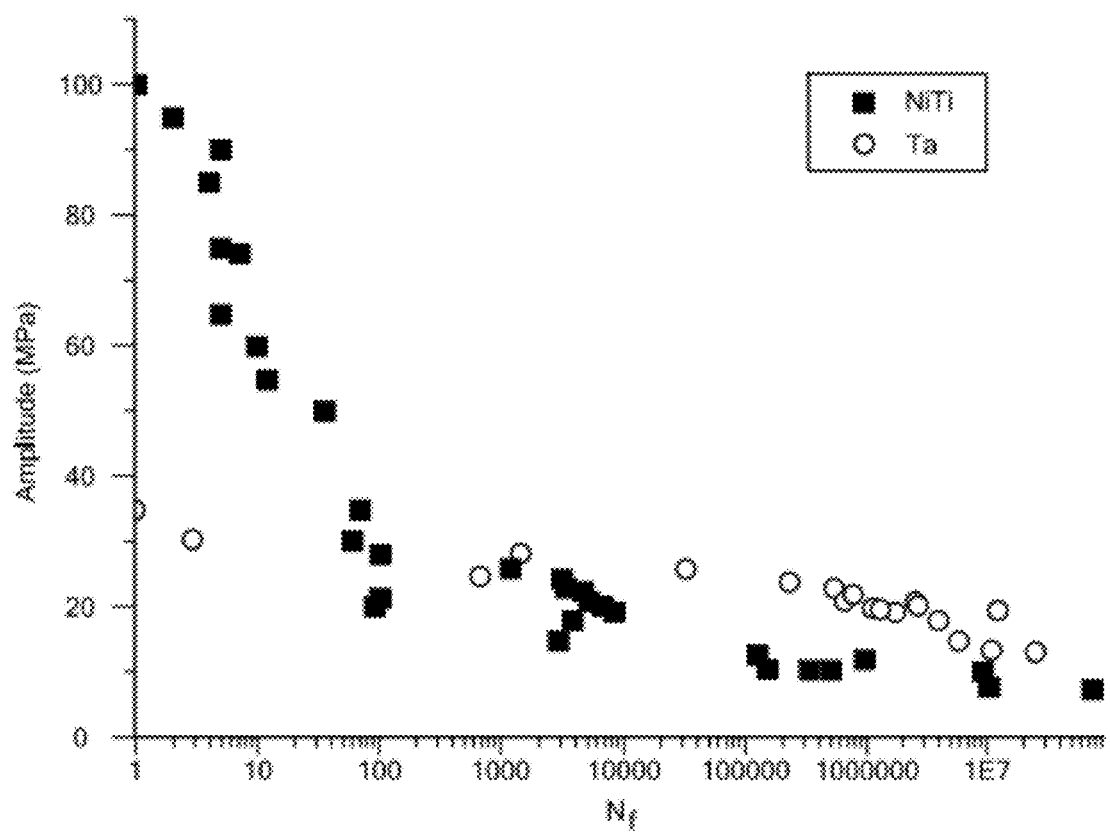
FIG. 10 is a chart showing output of the finite element model in accordance with the model of FIG. 9.

FIG. 10 shows the fatigue curve for Nitinol. Tables 2 and 3 show the results of the fatigue analysis for Nitinol in comparison to Cobalt Chromium, Titanium and Stainless Steel.

The expected life of the Nitinol implants is much less than the other materials, although the maximum von Mises stress values were much less.

The von Mises stress values for the austenitic and martensitic Nitinol were less than the CoCr, Ti, and SS. The maximum stress values occurred proximal to the region of fixation. The maximum stress for the austenitic Nitinol was higher than the martensitic. The modulus of elasticity for the low temperature Nitinol was roughly 40% of that of the high temperature.

The fatigue lives show a significant decrease in Nitinol than other materials. The expected number of cycles until failure was estimated from the SN curve of FIG. 10. The expected number of years before failure for the Nitinol design was estimated to be between 0.07 and 37 years, which was clearly less than for comparable CoCrMo and stainless steel (SS) prostheses.

TABLE 1

List of properties used for the analyses

| Material | Modulus of Elasticity (E) $10^6$ psi | Poissons Ratio (n) |
|---|---|---|
| Bone | 0.5 | 0.30 |
| CoCrMo | 25 | 0.29 |
| Nitinol (Austenite) | 10.9 | 0.30 |
| Nitinol (Martensite) | 4.06 | 0.30 |

TABLE 2

Fatigue results for a SF = 1.0

| SF = 1.0 | Hip A yrs | Hip B yrs |
|---|---|---|
| CoCrMo | 100.0 | 100.0 |
| SS | 100.0 | 100.0 |
| Ti | 100.0 | 100.0 |
| Nitinol (Austenite) | 37.0 | 6.05 |
| Nitinol (Martensite) | 33.9 | 6.05 |

TABLE 3

Fatigue results for a SF = 1.5

| SF = 1.5 | Hip A yrs | Hip B yrs |
|---|---|---|
| CoCrMo | 22.9 | 100.0 |
| SS | 100.0 | 100.0 |
| Ti | 100.0 | 87.7 |
| Nitinol (Austenite) | 4.76 | 0.07 |
| Nitinol (Martensite) | 3.43 | 0.07 |

Example 2

Finite Element Modeling of an Implant According to FIG. 1a

To confirm the hypothesis that a short-stemmed Nitinol prosthesis 100 with a lateral flare according to FIG. 1a would be sufficiently robust, further finite element modeling was performed to simulate the fatigue endurance strength properties of a short-stemmed prosthesis. A quasi-static analyses was performed with the commercial finite element analysis (FEA) code ABAQUS/Standard version 6.5-1. Three dimensional elements and a large displacement formulation were used. Two material models were used for this report: the first was a Nitinol material model assuming a superelastic response with an $A_f$ temperature of 30° C. and a typical stainless steel material with approximately 20% cold work was chosen as a baseline for comparison. Two finite element models were created to examine the effect of mesh refinement on the accuracy of the solution. The number of degrees of freedom for the base model and the fine model were 44853 and 111138, respectively. The difference in the results between the two models was considered negligible, so a mesh with refinement consistent with the base mesh was selected. Following the ISO+7206-4-2002 testing standard, the load path was determined by defining the axis of the hip implant using 0.1 and 0.4 CT distances (CT is the distance from the tip of the implant to the center of the implant head) and offsetting this by 10 degrees (alpha in Table 1 of the ISO standard). This was the on axis loading scenario. The implant was embedded to a depth of 0.4 CT from the center of the ball. The effect of the boundary conditions in the location of the embedded material was examined and it was found that there was no effect on the location of the maximum stresses and strains near the head of the implant. Following standard ISO+7206-4-2002, off axis loading was defined following the procedure for on axis loading with an additional rotation of the load path by 9 degrees from the plane of the hip implant (beta in Table 1 of the ISO standard). The following table summarizes the results for the on axis and off axis load cases considered.

TABLE 4

Summary of the results.

| Load Case | Material | Load Max [kN] | Maximum Principal Strain [percent] | vonMises Stress [MPa] |
|---|---|---|---|---|
| On Axis | Nitinol | 2.5 | 0.264 | 119 |
| | Stainless Steel | 2.5 | 0.050 | 119 |
| Off Axis | Nitinol | 2.5 | 0.292 | 131 |
| | Stainless Steel | 2.5 | 0.056 | 131 |

The stresses for both the Nitinol and stainless steel prostheses when loaded to 2.5 kN were similar and below typical levels associated with survival to 10M cycles ("Metallic materials", J. R. Davis, editor, Handbook of Materials for Medical Devices, page 30. ASM International, 2003.). The strains for the Nitinol prosthesis were five times larger than for the stainless steel component, as would be expected based on the difference in elastic modulus for the two materials. However, the 0.25% strain experienced by the Nitinol component is still below typical values assumed for survival out to 400 million cycles (A. R. Pelton, X. Y. Gong, and T. W. Duerig, "Fatigue testing of diamond shaped specimens.", Proceedings of the International Conference on Superelastic and Shape Memory Technologies, 2003). A contour plot of vonMises stress for off axis loading of 2.5kN is shown in FIG. 11.

Several conclusions may be drawn in comparing the long-stemmed Nitinol prostheses of Example 1 with the abbreviated Nitinol prosthesis of example 2. For a long-stemmed prosthesis, the bending moment is applied through the intramedullary stem and results in stress concentrations at the medial and distal lateral ends of the prosthesis. The axial load and torsional moments are transferred to the bone across the bone-prosthesis interface, resulting in high interface shear stresses that may cause the stem to fracture due to fatigue. In contrast, the short-stemmed prosthesis locks proximally in the metaphysis and, as a result, significantly reduces or eliminates interface shear stresses in the intramedullary canal. The short-stem has no bending moments in the diaphysis, but bears axial and compressive loads in the metaphysis. The active locking force of the short-stemmed prosthesis will provide torsional support and anchoring while increasing the physiological loading of the proximal femur. The result is a more natural stress distribution across a proximal femur cross section. Thus stress-shielding may be effectively minimized, and concerns about fatigue failure due to bending moments of the stem are reduced or removed.

In an alternative embodiment, pseudoelastic shape-memory material is used without a temperature-induced transition to cause a locking-force. The prosthesis 100 has a pseudoelastic bone-locking portion with an $A_f$ that is below 37° C. (e.g. $A_f$=30° C.). In this case the pseudoelastic prosthesis may be inserted forcibly into the aperture (e.g., with a hammer). The resiliency of the pseudoelastic material will then provide the locking force. In a related embodiment, the pseudoelastic prosthesis is constrained by a rigid sleeve (e.g., a hard plastic sleeve). After insertion of the constrained prosthesis into the bone aperture, the sleeve is removed. The prosthesis may be coated or wrapped with a gap-filling material such as collagen before insertion into the sleeve. After removing the sleeve, the gap-filling material will bridge the bone-prosthesis interface. Use of the sleeve may avoid or mitigate the need for forcible insertion into the aperture and will protect any coatings or gap filling materials from scraping forces.

In another embodiment, the shape-memory material does change phase in response to a temperature change, but only partially. For example, a shape memory material with a wide transition temperature range that overlaps body temperature may be employed.

A further embodiment includes a method of revising a prosthesis implantation. A prosthesis with a 2-way shape-memory bone-locking portion is cooled to induce formation of martensite that is sufficient to loosen the prosthesis so that it may be removed with minimal damage to the bone.

The described embodiments of the invention are intended to be merely exemplary and numerous variations and modifications will be apparent to those skilled in the art. All such variations and modifications are intended to be within the scope of the present invention as defined in the appended claims.

What is claimed is:

1. A femoral stem hip implant for insertion into a surgically created aperture in a femur, the implant comprising:
a monolithic femoral stem made of shape memory material, the stem configured to be inserted into the aperture, the stem having a proximal portion and a longitudinal axis, the shape memory material within the proximal portion having a cross-section perpendicular to the longitudinal axis, at least a portion of the shape memory material within the proximal portion being in a compressed state by application of a plurality of compressive forces at a temperature below an austenitic finish temperature of the shape memory material so that the cross-section of the shape memory material expands through shape memory effect via the formation of austenite in response to a temperature increase after insertion into the aperture thereby causing a locking-force to be exerted against an inner surface of the aperture, the locking force being sufficient to stabilize the implant in the aperture, wherein at least 70% of the cross-section is occupied by shape memory material.

2. A femoral stem hip implant for insertion into a surgically created aperture in a femur, the implant comprising:
a monolithic femoral stem made of shape memory material, the stem configured to be inserted into the aperture, the stem having a proximal portion and a longitudinal axis, the shape memory material within the proximal portion having a cross-section perpendicular to the longitudinal axis, at least a portion of the shape memory material within the proximal portion being in a compressed state by application of a plurality of compressive forces at a temperature below an austenitic finish temperature of the shape memory material so that the cross-section of the shape memory material expands through shape memory effect via the formation of austenite in response to a temperature increase after insertion into the aperture thereby causing a locking-force to be exerted against an inner surface of the aperture, the locking force being sufficient to stabilize the implant in the aperture, wherein the entirety of the cross-section is occupied by shape memory material.

* * * * *